(12) United States Patent
Nakata

(10) Patent No.: US 11,948,397 B2
(45) Date of Patent: Apr. 2, 2024

(54) ELECTRONIC DEVICE

(71) Applicant: SONY SEMICONDUCTOR SOLUTIONS CORPORATION, Kanagawa (JP)

(72) Inventor: Masashi Nakata, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 0 days.

(21) Appl. No.: 17/906,338

(22) PCT Filed: Feb. 18, 2021

(86) PCT No.: PCT/JP2021/006194
§ 371 (c)(1),
(2) Date: Sep. 14, 2022

(87) PCT Pub. No.: WO2021/199768
PCT Pub. Date: Oct. 7, 2021

(65) Prior Publication Data
US 2023/0177867 A1    Jun. 8, 2023

(30) Foreign Application Priority Data
Mar. 30, 2020  (JP) .................. 2020-061494

(51) Int. Cl.
*G06V 40/13* (2022.01)
*G06F 21/32* (2013.01)
(Continued)

(52) U.S. Cl.
CPC .......... *G06V 40/1318* (2022.01); *G06F 21/32* (2013.01); *G06Q 30/0641* (2013.01);
(Continued)

(58) Field of Classification Search
CPC .......... G06V 40/1318; G06V 40/1365; G06V 40/15; G06V 40/67; G06V 40/1335;
(Continued)

(56) References Cited

U.S. PATENT DOCUMENTS

2012/0258773 A1  10/2012  Alvarez Rivera et al.
2014/0355845 A1* 12/2014  Benkley ............. G06V 40/1335
382/124

(Continued)

FOREIGN PATENT DOCUMENTS

JP      07-334646 A    12/1995
JP   2000-020684 A     1/2000
(Continued)

OTHER PUBLICATIONS

International Search Report and Written Opinion of PCT Application No. PCT/JP2021/006194, dated Apr. 20, 2021, 11 pages of ISRWO.

*Primary Examiner* — Premal R Patel
(74) *Attorney, Agent, or Firm* — CHIP LAW GROUP

(57) ABSTRACT

Fingerprint authentication is realized during a swipe operation of a display. An electronic device includes a display, an optical fingerprint sensor, and an information processing unit. The display includes a display surface having light emitting pixels in an array in a first direction and a second direction intersecting the first direction. The optical fingerprint sensor includes an imaging element having light receiving elements in an array in a first direction and a second direction on a side opposite to the display surface of the display in a third direction intersecting the first direction and the second direction, and acquires fingerprint information of fingerprint moving in contact with the display. The
(Continued)

information processing unit acquires corrected fingerprint information from the fingerprint information acquired by the optical fingerprint sensor.

19 Claims, 13 Drawing Sheets

(51) Int. Cl.
*G06Q 30/0601* (2023.01)
*G06V 40/10* (2022.01)
*G06V 40/12* (2022.01)
*G06V 40/60* (2022.01)

(52) U.S. Cl.
CPC .......... *G06V 40/1365* (2022.01); *G06V 40/15* (2022.01); *G06V 40/67* (2022.01)

(58) Field of Classification Search
CPC ........ G06F 21/32; G06F 3/0488; G06F 18/00; G06Q 30/0641; A61B 5/1172; G06T 1/00
See application file for complete search history.

(56) References Cited

U.S. PATENT DOCUMENTS

| | | | | |
|---|---|---|---|---|
| 2019/0034697 A1* | 1/2019 | Matsunami | ........ | G06V 40/1365 |
| 2020/0111851 A1* | 4/2020 | Park | ........ | H10K 39/32 |
| 2020/0184246 A1* | 6/2020 | Fan | ........ | G06V 40/1318 |
| 2020/0234020 A1* | 7/2020 | Yoon | ........ | G06V 40/1359 |

FOREIGN PATENT DOCUMENTS

| | | |
|---|---|---|
| JP | 2003-248820 A | 9/2003 |
| JP | 2008-006146 A | 1/2008 |
| JP | 2009-064262 A | 3/2009 |
| JP | 2017-538225 A | 12/2017 |
| JP | 2019-028490 A | 2/2019 |
| JP | 2019-128961 A | 8/2019 |
| WO | 2005/069212 A1 | 7/2005 |

* cited by examiner

OUTER APPEARANCE VIEW        CROSS-SECTIONAL VIEW

THIRD
DIRECTION

ELECTRONIC DEVICE

CROSS REFERENCE TO RELATED APPLICATIONS

This application is a U.S. National Phase of International Patent Application No. PCT/JP2021/006194 filed on Feb. 18, 2021, which claims priority benefit of Japanese Patent Application No. JP 2020-061494 filed in the Japan Patent Office on Mar. 30, 2020. Each of the above-referenced applications is hereby incorporated herein by reference in its entirety.

TECHNICAL FIELD

The present disclosure relates to an electronic device.

BACKGROUND ART

In the optical fingerprint sensor, it is necessary to stop the finger for a predetermined time at the time of acquiring the fingerprint, and the convenience is low from the viewpoint of the UI. Furthermore, in a terminal that has logged in by fingerprint authentication, a subsequent operation is often possible without performing fingerprint authentication and the like. For example, it is often possible to perform shopping by credit card payment from a browser after performing personal authentication by fingerprint once, and there is also a security problem.

CITATION LIST

Patent Document

Patent Document 1: US 2012/0258773 A

SUMMARY OF THE INVENTION

Problems to be Solved by the Invention

One aspect of the present disclosure provides an electronic device that implements fingerprint authentication during a swipe operation of a display.

Solutions to Problems

According to an embodiment, the electronic device includes a display, an optical fingerprint sensor, and an information processing unit. The display includes a display surface having light emitting pixels in an array in a first direction and a second direction intersecting the first direction. The optical fingerprint sensor includes an imaging element having light receiving elements in an array in a first direction and a second direction on a side opposite to the display surface of the display in a third direction intersecting the first direction and the second direction, and acquires fingerprint information of fingerprint moving in contact with the display. The information processing unit acquires corrected fingerprint information from the fingerprint information acquired by the optical fingerprint sensor.

The information processing unit may correct the fingerprint information acquired during an operation including at least a finger swipe operation.

A touch panel configured to sense contact information on the display may be further included. The information processing unit may estimate an operation speed from the contact information and acquire the corrected fingerprint information on the basis of the operation speed.

The information processing unit may select one of the fingerprint information in the fingerprint information of a plurality of frames, and aggregate the fingerprint information of another frame to the selected fingerprint information.

The information processing unit may determine an exposure time of the optical fingerprint sensor on the basis of the estimated operation speed.

The information processing unit may determine a reading direction of the imaging element in the optical fingerprint sensor on the basis of a direction of the estimated operation speed.

An instruction to slow down a speed of the swipe operation may be output on the basis of the requested authentication accuracy.

An instruction of the speed of the swipe operation may be output to the display.

The instruction may display a speed guide on the display.

In a case where the speed is faster than a predetermined speed, it may be output that the speed is too fast.

The output that the speed is too fast may be at least one of an output to the display, an output in sound, or an output in vibration.

The information processing unit may shorten an exposure time of the optical fingerprint sensor in a case where the speed is faster than a predetermined speed.

The light emitting pixel may output light of different wavelengths on the display surface side of the light receiving element, and the light receiving element may acquire the fingerprint information on the basis of reflected light of different wavelengths.

A polarizing filter may be included between the light receiving element and the display surface, and the light receiving element may sense polarized light through the polarizing filter.

A filter configured to acquire a state of hemoglobin may be included between the light receiving element and the display surface, and the information processing unit may acquire information of the hemoglobin and perform biometric authentication.

The information processing unit may perform biometric authentication on the basis of information on a temporal shape change of a finger in contact with the display surface.

The light receiving element may detect operations of a plurality of fingers.

The information processing unit may execute the fingerprint authentication using a combination of a plurality of fingers in the operations of the plurality of fingers.

The combination of the plurality of fingers may be different on the basis of a requested authentication accuracy.

The information processing unit may detect finger information and accumulate the fingerprint information during execution of authentication or during non-execution of authentication.

The information processing unit may improve authentication accuracy by accumulating changes of a finger.

The information processing unit may acquire and accumulate the fingerprint information of a finger other than an unregistered finger.

In the light receiving elements, a number of elements in a direction intersecting a direction of the swipe operation may be larger than a number of elements in the direction of the swipe operation.

In the light receiving elements, a number of elements in a direction intersecting a direction of the swipe operation may be larger than twice a number of elements in the direction of the swipe operation.

A guide on which the swipe operation is executed in a direction intersecting a direction in which a large number of the light receiving elements are provided may be displayed on the display.

On the display, a region in which the light receiving element is provided may be displayed, and product information and a purchase button may be disposed so as to pass through the region. An interface that enables purchase of the product by the swipe operation of the product information from the product information to the purchase button may be provided, and the purchase information may be transmitted to a server on the basis of a result of the fingerprint authentication.

A dynamic object may be displayed on the display so as to include a region in which the light receiving element is provided.

The shape of the object may change when a user's finger touches the object.

A light emission state of the object may change when a user's finger touches the object.

The light emission state may change so as to be suitable for obtaining the fingerprint information.

The object may dynamically change on the basis of an acquisition status of the fingerprint information or a personal authentication status after a user's finger passes through the object.

An inclination detection unit configured to detect an inclination of the display from a horizontal direction may be further included, and authentication of the fingerprint information may be executed on the basis of the inclination detected by the inclination detection unit.

The optical fingerprint sensor may acquire the fingerprint information at a frame rate higher than a transfer rate to the information processing unit, and transfer the fingerprint information to the information processing unit in a case where the fingerprint information has an information amount of a predetermined information amount or more.

An imaging speed of the optical fingerprint sensor may be a frame rate of 100 frame per second (FPS) or more.

In the optical fingerprint sensor, an amount of data included in the fingerprint information may be estimated, and in a case where the amount of data exceeds a predetermined value, the fingerprint information may be transferred to the information processing unit.

The optical fingerprint sensor may estimate the amount of data by image analysis.

The optical fingerprint sensor may estimate the amount of data on the basis of information of a touch panel.

MODE FOR CARRYING OUT THE INVENTION

Hereinafter, an embodiment of an electronic device will be described with reference to the drawings. Although main components of the electronic device will be mainly described below, the electronic device may have components and functions that are not illustrated or described. The following description does not exclude components and functions that are not illustrated or described. Furthermore, there are cases where the size, shape, aspect ratio, and the like are changed for the sake of explanation, but these have an appropriate size, shape, aspect ratio, and the like in mounting.

Note that, in the following description, a signal to be acquired is described as image information or imaging information, but the image information and the imaging information are concepts in a broad sense, and are concepts including an image of one frame in a still image, a moving image, or a video. Furthermore, "larger" and "smaller" may be read as "equal to or more" and "equal to or less", respectively.

First Embodiment

Figure 1:
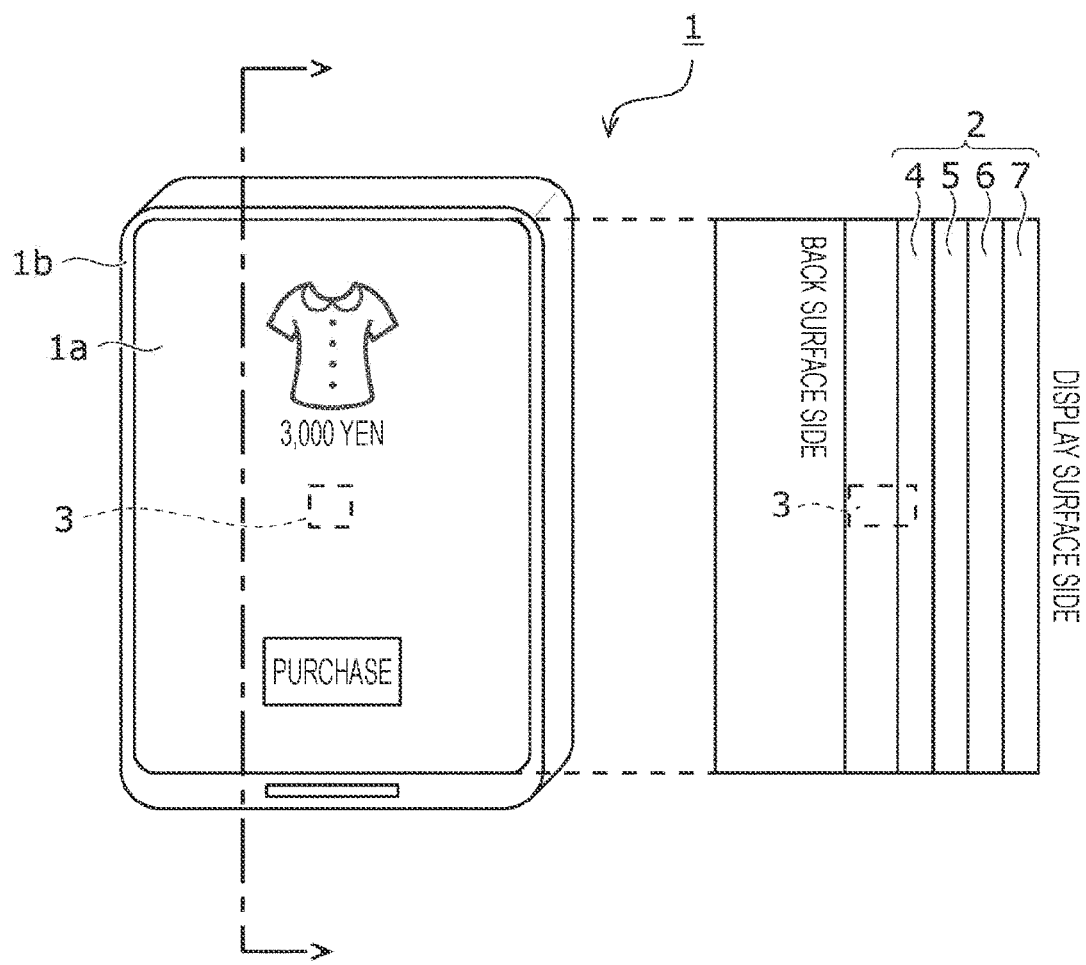
FIG. 1 is a diagram schematically illustrating an electronic device according to an embodiment.
Figure 1:
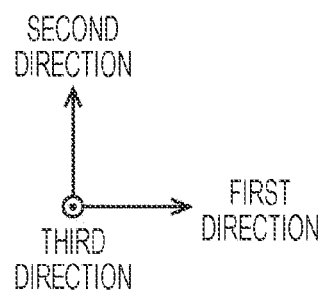
Figure 1:
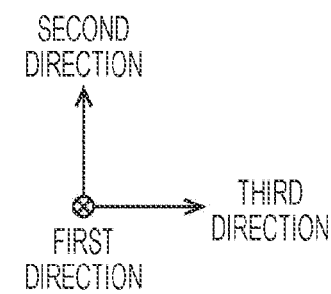
Figure 2:
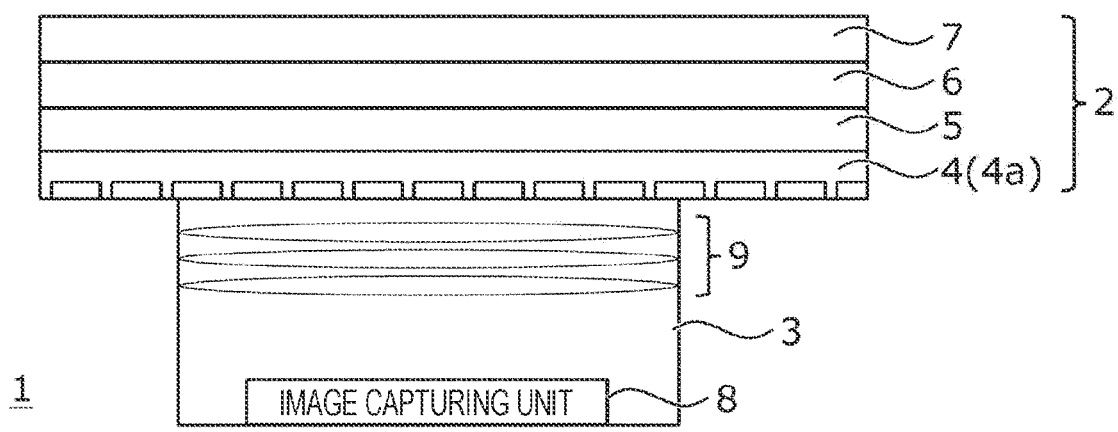
FIG. 2 is a diagram schematically illustrating a cross-sectional view of an electronic device according to an embodiment.

FIG. 1 is a diagram schematically illustrating an electronic device according to an embodiment. Furthermore, FIG. 2 is a diagram schematically illustrating a cross section of the electronic device according to the embodiment. An electronic device 1 is an arbitrary device having a display function and an imaging function, for example, a smartphone, a mobile phone, a tablet terminal, a personal computer, and the like.

The electronic device 1 includes a display unit 2 and a camera module 3. As can be seen in the left diagram of FIG. 1, a display screen 1a extends close to the outer size of the electronic device 1, and the width of a bezel 1b around the display screen 1a can be set to several mm or less, for example. In many electronic devices 1, a fingerprint authentication unit is provided in the bezel 1b, but in the present embodiment, the camera module 3 is provided in the display screen 1a as indicated by a dotted line. As illustrated in the left diagram, the width of the bezel 1b can be narrowed by providing the camera module 3 on the back surface side of the display screen 1a, the camera module 3 imaging for fingerprint authentication.

Note that, in FIG. 1, the camera module 3 is disposed on the back surface side around substantially the center of the display screen 1a, but the position is not limited to this diagram as long as it is the back surface of the display screen 1a. For example, the camera module 3 may be disposed near the peripheral portion of the display screen 1a, or may be disposed below the center of the right diagram. Furthermore, although one place is disposed in the diagram, the arrangement place may be not one place but a plurality of places. Furthermore, in this drawing, the display unit 2 and the camera module 3 are provided on one surface of the electronic device 1, but the present invention is not limited thereto. For example, the display unit 2 and the camera module 3 may be provided on both surfaces of the electronic device 1.

The display unit 2 is a structure in which a display panel 4, a circularly polarizing plate 5, a touch panel 6, and a cover glass 7 are stacked as a display optical system. Note that the arrangement of these components is not limited, and may be appropriately replaced. Two or more of the same configuration may be present, or another configuration may be included.

The display panel 4 may include, for example, an organic light emitting diode (OLED), a liquid crystal, a micro LED, and other light emitting elements based on a display principle in an array. For example, the light emitting elements are provided in an array in a plane including a first direction and a second direction. The display panel 4 such as an OLED is configured by a plurality of layers. A member having low transmittance such as a color filter layer is often disposed on the display panel 4. As described later, a through hole may be formed in a member having a low transmittance in the display panel 4 in accordance with an arrangement place of the camera module 3. If the object light passing through the through hole is made incident on the camera module 3, the image quality of the image captured by the camera module 3 can be improved.

The circularly polarizing plate 5 is provided to reduce glare, enhance visibility of the display screen 1a, and the like even in a bright environment. A touch sensor is incorporated in the touch panel 6. There are various types of touch sensors such as a capacitive type, a resistive film type, and a pressure-sensitive type, but any type may be used. Furthermore, the touch panel 6 and the display panel 4 may be integrated. The cover glass 7 is provided to protect the display panel 4 and the like. Each of these elements may be bonded by an optically less influential adhesive.

The camera module 3 includes an image capturing unit 8 and an optical system 9. The optical system 9 is disposed on the light incident surface side of the image capturing unit 8, that is, on the side close to the display unit 2, and condenses the light passing through the display unit 2 on the image capturing unit 8. The optical system 9 may include one or a plurality of lenses. For example, the image capturing unit 8 operates as an optical fingerprint sensor to acquire fingerprint information of the user.

The image capturing unit 8 operating as an optical fingerprint sensor includes a plurality of photoelectric conversion units. A lens is disposed in each photoelectric conversion unit. This lens causes the photoelectric conversion unit constituting each pixel to receive light appropriately emitted to the image capturing unit 8 by the optical system 9. The photoelectric conversion unit photoelectrically converts light incident through the display unit 2. The photoelectric conversion unit may be a complementary metal-oxide-semiconductor field-effect transistor (CMOS) sensor or a charge coupled device (CCD) sensor. The photoelectric conversion units are provided in an array on a plane including the first direction and the second direction, for example. Furthermore, the photoelectric conversion units may be provided in an array along the first direction and the second direction. For example, the light receiving element of the photoelectric conversion unit is provided as an array-like light receiving pixel along the same direction as the light emitting pixel of the display unit.

Furthermore, the photoelectric conversion unit may include a photodiode or an organic photoelectric conversion film. The plurality of photoelectric conversion units can be arranged in any manner. The method for arranging the plurality of photoelectric conversion units may be, for example, a Bayer array, an interline array, a checkered array, a stripe array, or another array.

In the present disclosure, an output value of the photoelectric conversion unit or a value subjected to predetermined conversion on the basis of the output value is referred to as a light receiving pixel value.

In the present embodiment, the fingerprint information of the user is acquired at a timing when a finger passes through a region where the camera module 3 of the display is present, and personal authentication is executed using the fingerprint information. For example, as illustrated in the left diagram of FIG. 1, in a case where product information and a purchase button are displayed on the display, the camera module 3 acquires the fingerprint information from the finger being swiped, flicked, wiped, and the like at the timing of dragging the image of the product to the purchase button. This acquisition is executed using a rolling shutter as described later. Furthermore, the camera module 3 executes the operation of the rolling shutter in an appropriate exposure time.

Figure 3:
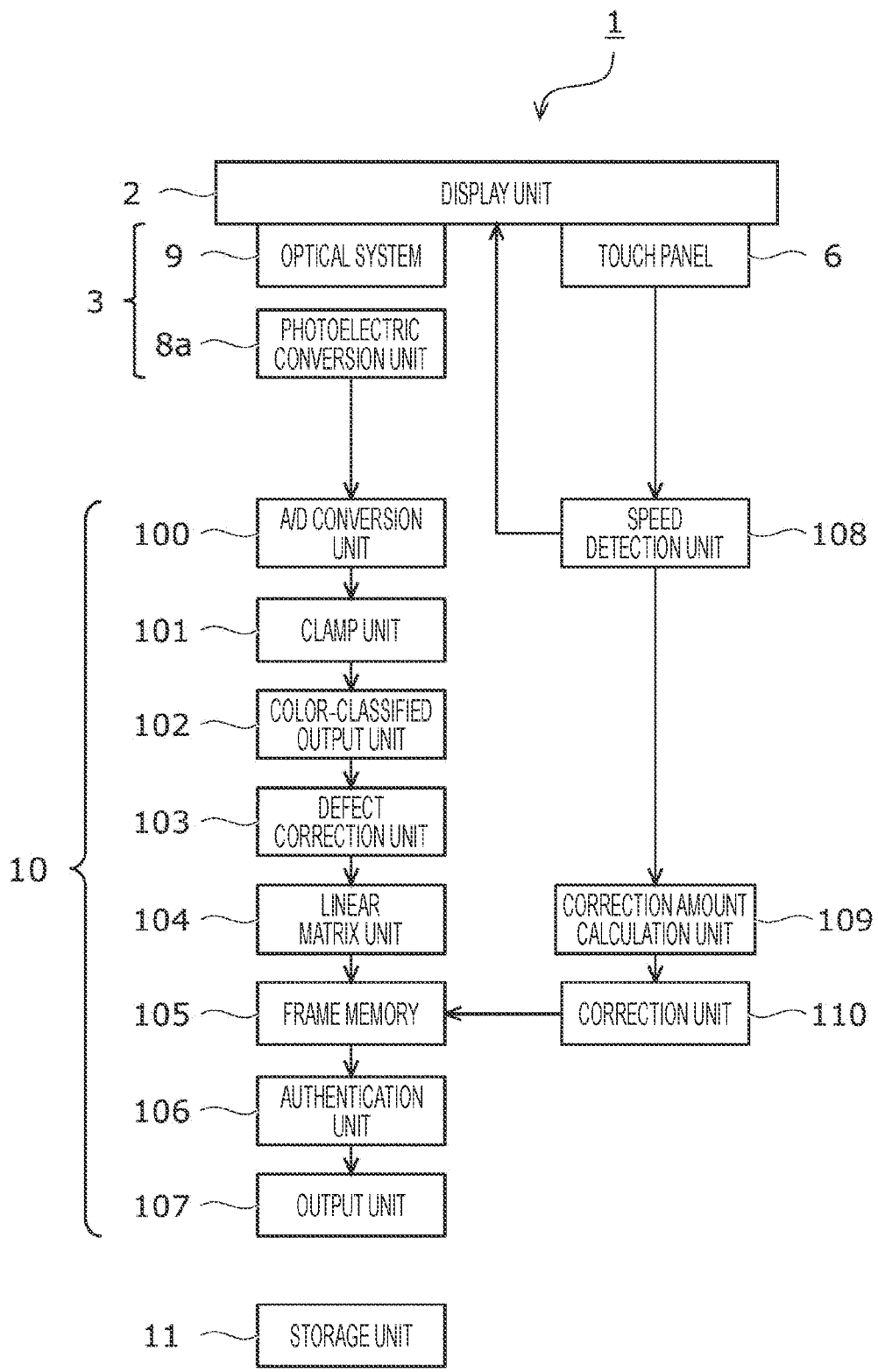
FIG. 3 is a block diagram illustrating an example of a configuration of an electronic device according to an embodiment.

FIG. 3 is a diagram illustrating an example of a block diagram of the electronic device 1 according to the present embodiment. The inside of the display unit 2 illustrated in FIGS. 1 and 2 is omitted. The electronic device 1 includes an information processing unit 10 that outputs information from the camera module 3 and the touch panel 6 described above and executes this information processing, and a storage unit 11.

The image capturing unit 8 of the camera module 3 includes a photoelectric conversion unit 8a (photoelectric conversion element). The information sensed by the photoelectric conversion unit 8a is transferred to the information processing unit 10 at the timing of each line, for example.

The information processing unit 10 is configured by, for example, a central processing unit (CPU), an application specific integrated circuit (ASIC), a field programmable gate array (FPGA), and the like. As described below, the information processing unit 10 may be divided into blocks that perform some or all of various operations, or information processing by software for some or all of the operations may be specifically implemented by the CPU.

The storage unit 11 includes, for example, various memories, storages, and the like. For example, information such as programs and data necessary for the operation of the electronic device 1 may be non-temporarily stored in the storage unit 11. Furthermore, the memory may include a temporary storage area such as a cache area.

The information processing unit 10 includes an A/D conversion unit 100, a clamp unit 101, a color-classified output unit 102, a defect correction unit 103, a linear matrix unit 104, a frame memory 105, an authentication unit 106, an output unit 107, a speed detection unit 108, a correction amount calculation unit 109, and a correction unit 110. The frame memory 105 may be provided as a part of the storage unit 11 instead of the information processing unit 10.

The A/D conversion unit 100 converts an analog signal based on the charge received and stored by the photoelectric conversion unit 8a into a digital signal for each pixel. The A/D conversion unit 100 outputs the converted digital signal as image data.

For example, the clamp unit 101 defines a black level, subtracts the defined black level from the image data output from the A/D conversion unit 100, and outputs the image data. The clamp unit 101 may set a ground level for each photoelectric conversion element included in the pixel. In this case, the ground correction of the signal value is executed on the basis of the acquired ground level set for each photoelectric conversion element.

For example, in a case where the photoelectric conversion unit 8a acquires an analog signal for each color, the color-classified output unit 102 outputs data of the subpixel image for each color. The photoelectric conversion unit 8a includes, for example, color filters of red (R), green (G), and blue (B). Each photoelectric conversion unit 8a outputs the sensed information for each color by these filters and the like. Instead of being provided with a color filter in the photoelectric conversion unit 8a, the photoelectric conversion unit 8a may acquire an analog signal for each color by an organic photoelectric conversion film.

The clamp unit 101 adjusts the ground level on the basis of these filters, and the color-classified output unit 102 outputs the signal output from the clamp unit 101 for each color. No color information is added to the analog signal acquired by the photoelectric conversion unit 8a. Therefore, the color-classified output unit 102 may store data regarding colors disposed for each light receiving element in the photoelectric conversion unit 8a, and may perform output for each color on the basis of the data.

Note that the photoelectric conversion unit 8a may include, for example, an element that receives near-infrared light, a filter that acquires a complex spectrum such as a plasmon filter, and the like. In these cases, it is difficult to express the information simply as color information, but the color-classified output unit 102 may process the information in association with the wavelength information as long as the information can be classified by the wavelength of light. In such a case, the color-classified output unit 102 may process the wavelength information as information having a range.

The defect correction unit 103 corrects a defect in the image data. The defect of the image data occurs, for example, due to a pixel defect or information defect due to a defect of a photoelectric conversion element provided in the pixel, due to information loss due to light saturation in the optical system 9, and the like. The defect correction unit 103 may execute defect correction processing by performing interpolation on the basis of, for example, information of surrounding pixels or information of surrounding pixels having the same color information.

The linear matrix unit 104 performs color reproduction by executing matrix calculation on the color information. For example, the linear matrix unit 104 acquires desired spectroscopy by performing calculation relating to a plurality of wavelengths. In the present embodiment, the linear matrix unit 104 may execute, for example, an output suitable for detecting a skin color. Moreover, in order to acquire biometric authentication information of veins and the like, the linear matrix unit 104 may execute calculation so as to obtain an output suitable for detection of a wavelength region from yellow to red.

As described above, the frame memory 105 may be provided as a part of the storage unit 11, for example. The frame memory 105 temporarily stores the information acquired from the photoelectric conversion unit 8a after the above processing is performed. For example, the information processing unit 10 performs various types of above processing on the fingerprint information acquired at the same timing in the frame memory 105, and finally stores the fingerprint information as one piece of image data color-reproduced by the linear matrix unit 104.

The authentication unit 106 executes personal authentication using the fingerprint information stored in the frame memory 105. For example, the personal authentication is executed by extracting a feature point in the fingerprint data and comparing the extracted feature point with the authentication information stored in the storage unit 11. Furthermore, the authentication unit 106 may execute biometric authentication for impersonation prevention on the basis of not only RGB information but also, for example, light reception information of near infrared rays and information acquired via a plasmon filter. For example, the biometric authentication is executed according to whether or not the information on the wavelength corresponding to hemoglobin in the data stored in the frame memory 105 is normally acquired. The feature points and the like may be determined by statistical processing, or authentication may be performed using a neural network model trained by machine learning as another example.

For example, the authentication unit 106 stores the fingerprint information of a specific user acquired in advance in the storage unit 11. The personal authentication is executed on the basis of the stored user information. In the case of authenticating a plurality of users, fingerprint information of the plurality of users is appropriately stored. Furthermore, in the stored fingerprint information, an image of each fingerprint information or information of a feature point acquired from each fingerprint information may be encrypted.

The output unit 107 outputs an authentication result by the authentication unit 106. For example, in the case of shopping by e-commerce and the like, the information may be transmitted to a server and the like so as to perform settlement processing on the basis of the authentication result. In this manner, the output unit 107 may transmit the authentication result by using wireless communication. Furthermore, as another example, in the electronic device 1, an authentication result such as fingerprint authentication may be used instead of authentication using a password and the like.

For example, the speed detection unit 108 acquires the speed of the motion of the user's finger at the timing when the camera module 3 acquires the image of the fingerprint on the basis of the sensing information of the touch panel 6. That is, in a case where the user performs a swipe operation, the camera module 3 acquires fingerprint information from light reception information, and the touch panel 6 acquires finger speed information from the sensed information. For example, the speed detection unit 108 acquires the speed of the finger on the basis of the moving amount of the region of the user's finger sensed by the touch panel 6 within a predetermined time.

The speed detection unit 108 acquires information for speed sensing from the touch panel 6, for example, in a case where a user's finger touches the touch screen at the timing of performing authentication. For example, in a case where the user's finger moves, the speed detection unit 108 acquires the sensing information of the touch panel 6 at a certain time and the sensing information of the touch panel 6 after a predetermined time.

For example, in a case where the region of the finger is sensed, the sensing information of the touch panel 6 may be acquired from the center point of the region of the finger, for example, the position of the center of gravity. The position of the center of gravity can be obtained, for example, by calculating an average of the points in the sensing region in the first direction and the second direction. Then, the speed detection unit 108 detects the swipe speed of the user's finger by obtaining the position of the center of gravity at a certain time and a predetermined time later.

The correction amount calculation unit 109 acquires a correction amount based on the speed detected by the speed detection unit 108. The image processing may be performed on the fingerprint information stored in the frame memory 105 on the basis of the correction amount. This image processing is, for example, image processing based on motion blur. The PSF may be generated on the basis of the speed of the finger and the shutter speed, and inverse filtering (deconvolution filtering) may be executed on the first fingerprint information.

The correction unit 110 executes the correction of the image data stored in the frame memory 105. This correction is executed on the basis of the correction amount calculated by the correction amount calculation unit 109. The calculation of the correction amount by the correction amount calculation unit 109 and the correction by the correction unit 110 will be described in detail later.

Figure 4A:
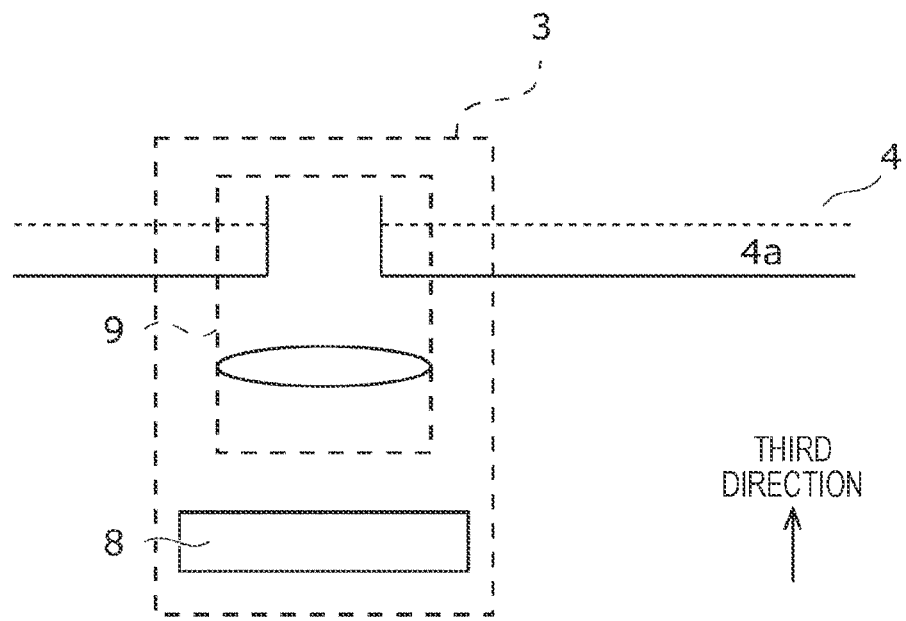
FIG. 4A is a diagram schematically illustrating a cross-sectional view of an electronic device according to an embodiment.

FIG. 4A is a diagram describing a relationship between the camera module 3 and the display panel 4 in FIG. 1 in more detail. As described above, the camera module 3 includes, for example, the image capturing unit 8 and the optical system 9. The optical system 9 is disposed on the light incident surface side of the image capturing unit 8, that is, on the side close to the display unit 2. The light transmitted through the display surface of the display unit 2 is propagated to the image capturing unit 8 by the optical system 9.

The image capturing unit 8 may include, for example, the photoelectric conversion unit 8a such as a photodiode illustrated in FIG. 3. The light condensed, refracted, diffused, and the like by the optical system 9 and propagated is received by the photoelectric conversion unit 8a included in the image capturing unit 8 and output as an analog signal. The photoelectric conversion unit 8a may include, for example, a color filter such as a Bayer array on the incident surface side of each imaging element, or may include a stacked color filter. Furthermore, other filters may be provided instead of the color filters as described above, or other elements such as an organic photoelectric conversion film may be configured. Furthermore, although not illustrated, an element, a circuit, and the like necessary for receiving light and outputting an analog signal are provided for the output.

For example, the optical system 9 may have a concept including a through hole in a member having a low transmittance. The through hole includes, for example, an aperture provided in the display panel 4, particularly, a substrate having a low transmittance in the display panel 4. The optical system 9 includes, for example, an aperture provided in the display panel 4 and a lens disposed at a position closer to the image capturing unit 8 than the aperture. With the lens and the aperture, in the optical system 9, optical characteristics such as numerical aperture (Na) and F-number in the camera module 3 may be defined.

Figure 4B:
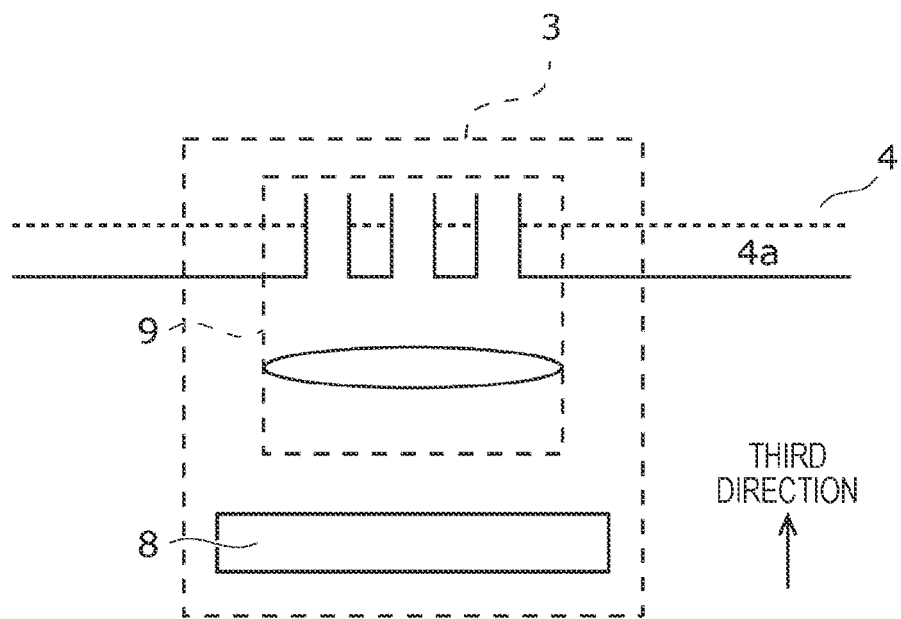
FIG. 4B is a diagram schematically illustrating a cross-sectional view of an electronic device according to an embodiment.

Note that the aperture and the lens are illustrated as an example, and the configuration of the optical system 9 is not necessarily limited to a combination thereof. Furthermore, in the drawing, one or a plurality of lenses is provided for one aperture, but the present invention is not limited thereto. For example, as illustrated in FIG. 4B, a plurality of apertures may be provided for one lens in the optical system 9. In the region where the aperture does not exist, for example, the light emitting element of the display panel 4 may be provided, and the aperture may be provided so as to be located between the light emitting elements. With this arrangement, the camera module 3 can be provided without losing the display.

The light receiving pixels disposed in an array in the image capturing unit 8 include, for example, the photoelectric conversion unit 8a described above. Note that the present disclosure is presented as an example, and thus a detailed description thereof will be omitted. Furthermore, the light receiving pixel in the present disclosure may be configured to operate as a rolling shutter.

To summarize FIGS. 1 to 3, the image capturing unit 8 may include an imaging element, in the third direction, which has light receiving elements in an array in the first direction and the second direction on the side opposite to the display surface of the display unit 2 that is a display. Then, each of these light receiving elements realizes an operation of a rolling shutter that sequentially reads light reception information. As described above, the information processing unit 10 executes signal processing of the fingerprint information read by the image capturing unit 8, that is, an optical fingerprint sensor. Then, for example, when the user slides his/her finger on the display surface of the display unit 2 (for example, a swipe operation is performed), fingerprint information is acquired by the optical fingerprint sensor, and personal authentication and the like can be executed. In the following, a swipe operation will be described. However, the movement is not limited to the swipe operation, and any motion such as flick or pinch may be used as long as the motion slides on the touch panel.

Figure 5:
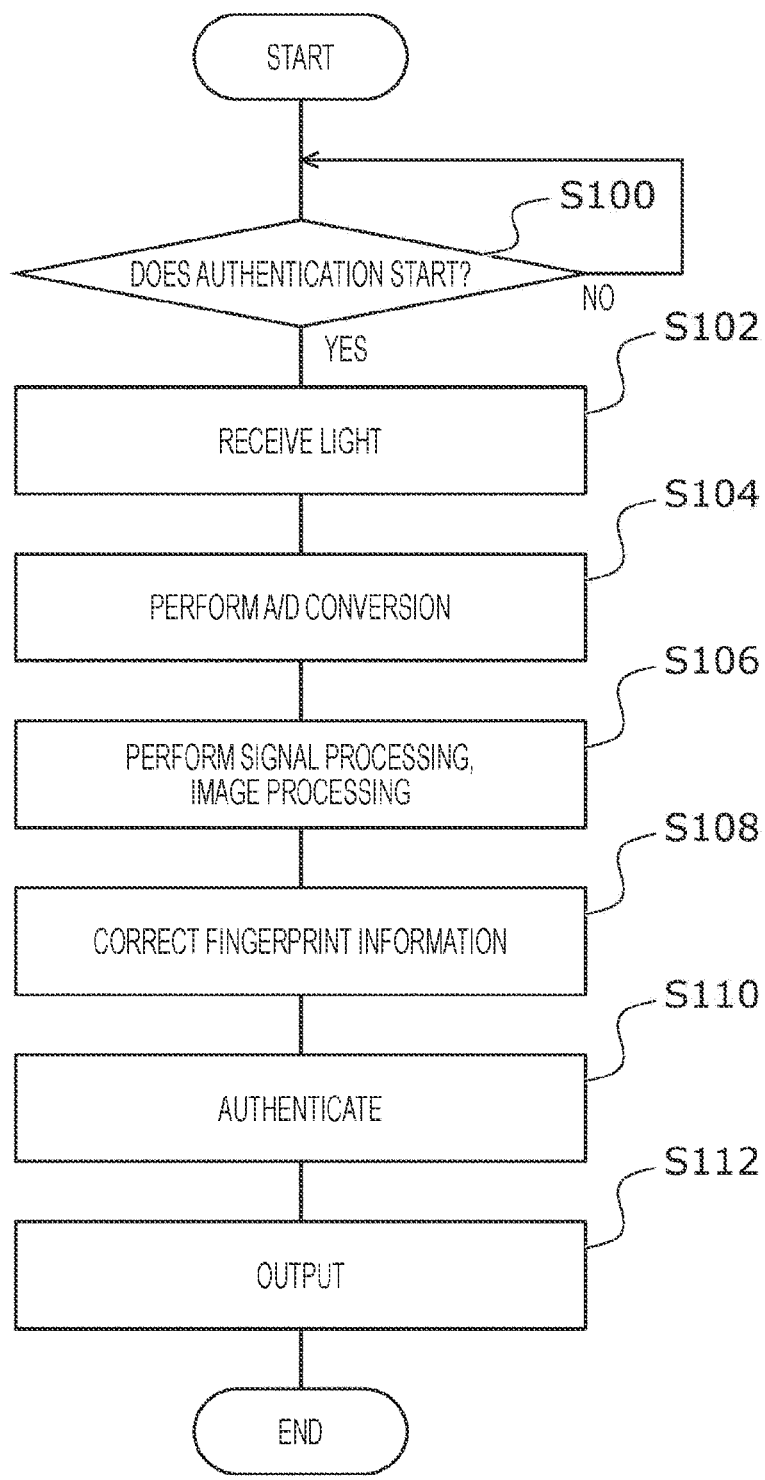
FIG. 5 is a flowchart illustrating processing of personal authentication according to an embodiment.

FIG. 5 is a flowchart of a personal authentication process according to an embodiment.

First, the electronic device 1 determines whether or not to start personal authentication (S100). When it is not the timing to start the personal authentication (S100: NO), the standby state is continued. For the start of authentication, for example, as indicated by a dotted line in FIG. 3, the sensed information of the touch panel 6 may be used. For example, after the sensed information on the touch panel 6 reaches the range of the camera module 3, the processing may shift to the fingerprint information acquisition processing. As a preceding stage, the electronic device 1 may be notified that the authentication process is executed in a web site and the like in order to perform authentication, and the electronic device 1 may be in the standby state.

In the authentication start state (S100: YES), the image capturing unit 8 starts light reception for personal authentication (S102). For example, by activating the camera module 3 for fingerprint authentication, the camera module 3 shifts to a standby state for acquisition of fingerprint information, and receives light at necessary timing. For example, charges are stored by photoelectric conversion of light received by the photoelectric conversion unit 8a, and output as an analog signal at a predetermined timing.

Next, the A/D conversion unit 100 performs A/D conversion of the analog signal acquired by the image capturing unit 8 (S104). Here, the analog signal output from the photoelectric conversion unit 8a is converted into a digital signal.

Next, the information processing unit 10 executes signal processing and image processing other than A/D conversion of the converted digital signal (S106). This processing is, for example, processing of clamping, color-by-color output, defect correction, color reproduction, and storage in the frame memory 105 as described above. Note that the above is an example, and further appropriate processing may be executed in addition to the above.

Figure 6:
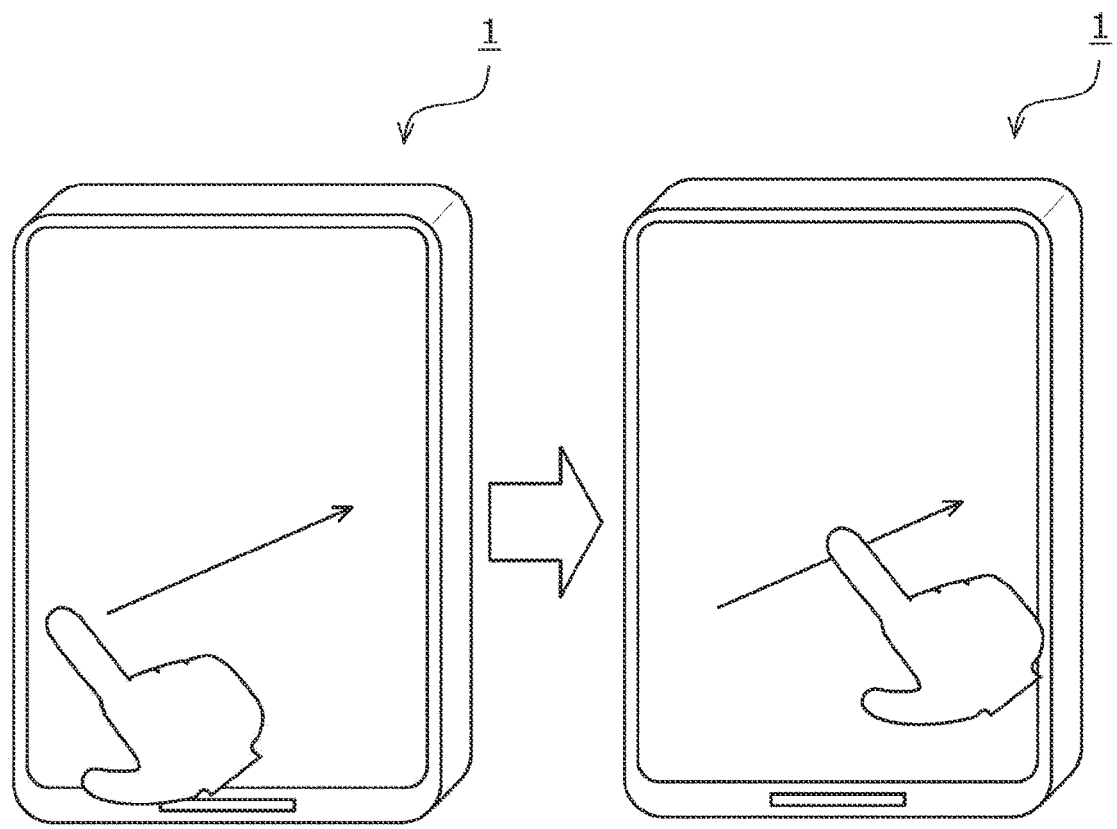
FIG. 6 is a diagram illustrating an example of a motion of a finger of a user according to an embodiment.
Figure 7:
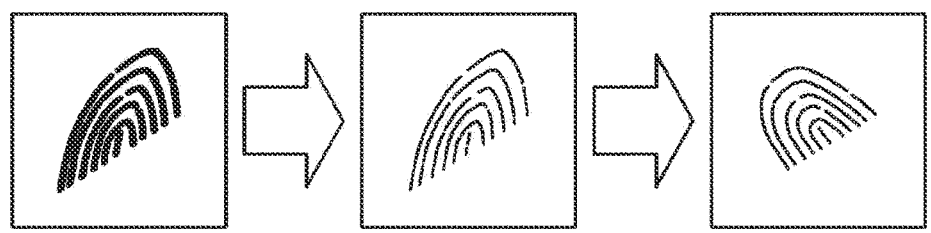
FIG. 7 is a diagram illustrating an example of image correction according to an embodiment.

Next, the correction unit 110 corrects the image information stored in the frame memory 105 (S108). FIG. 6 illustrates an example in which the user swipes in a certain direction while making contact on the display unit 2. As illustrated in the left diagram to the right diagram, the user executes the swipe operation in an arbitrary direction. FIG. 7 illustrates a fingerprint image captured at a certain timing acquired in this operation. Note that, in the present description, for example, it is assumed that reading of pixels from the image capturing unit 8 to the information processing unit 10 is executed from the bottom to the top in the drawing. The left side is an image indicating fingerprint information stored in the frame memory 105 in a photographed state. As illustrated in the left diagram, at this timing, there are image blur due to the shutter speed and global shutter distortion.

First, in the processing of S108, the speed detection unit 108 acquires information on the speed and direction of the motion of the user's finger at the timing from the touch panel 6. For example, the center of gravity of the sensed information of the touch panel 6 may be obtained, and the acquisition may be performed based on the positions of the centers of gravity with the frames before and after the timing. The correction amount calculation unit 109 calculates a correction amount on the basis of the detected speed. For example, on the basis of the values of the shutter speed and the speed, how much the finger itself deviates at the timing when the image of the left diagram is acquired is calculated. As a first stage of correction, the correction unit 110 estimates, for example, a point spread function (PSF) of motion blur with respect to the correction amount, and acquires a sharpened image by convolution filter processing. Note that it may be a process of sharpening simply by a morphology process, a Laplacian process, a Laplacian Gaussian process, and the like. Also in the case of these processes, the parameters of the matrix may be determined on the basis of the correction amount calculated by the correction amount calculation unit 109.

Next, the correction unit 110 executes rolling shutter distortion removal processing as a second stage of correction on the sharpened middle image. The correction unit 110 removes rolling shutter distortion on the basis of the correction amount calculated by the correction amount calculation unit 109 and the signal extraction timing of each line in the image capturing unit 8. Then, as illustrated in the right diagram, the correction unit 110 acquires the corrected fingerprint information that has been sharpened and from which the rolling shutter distortion has been removed. The correction unit 110 stores the corrected fingerprint information in the frame memory 105.

Next, the authentication unit 106 executes authentication using an image including the acquired fingerprint information (S110). For example, as described above, the authentication may be executed by extracting feature points and performing comparison processing, or may be performed using a trained neural network. Note that the electronic device 1 may include a chip capable of executing the information processing and the processing of the neural network described above in the same substrate as the camera module 3.

The output unit 107 outputs the authentication result to a necessary place (S112). For example, in the personal authentication in the case of shopping on the web, the personal authentication result may be notified to the browser that opens the web site or the application that receives the authentication result. In this manner, the output unit 107 can execute output to a necessary place.

For example, in a case where the authentication cannot be performed, the output unit 107 may notify that the authentication has failed to perform the authentication operation again. Furthermore, the output unit 107 may issue an imaging instruction to the image capturing unit 8 again.

In a case where images are acquired in consecutive frames, the authentication unit 106 may execute the authentication process using a plurality of pieces of fingerprint information. For example, when authentication can be performed in one of the plurality of fingerprint information, the output unit 107 may be notified that the authentication has succeeded at that timing.

In a case where authentication with high accuracy is required, the authentication unit 106 may change the authentication success/failure thresholds on the basis of the authentication accuracy. For example, in a case where high authentication accuracy is required, the authentication accuracy can be enhanced by increasing an authentication threshold, for example, a fingerprint matching degree threshold. In order to enhance the authentication accuracy, for example, a threshold of the matching degree of the feature points may be increased. Furthermore, in a case where the neural network model is used, the threshold of the matching degree may be increased. The case where authentication with high accuracy is required is, for example, when an expensive product is to be purchased, when information with high confidentiality is to be accessed, and the like.

Furthermore, in a case where the image capturing unit 8 includes a near-infrared filter, a plasmon filter, and the like, authentication as to whether or not the image capturing unit 8 is a living body may be performed together with personal authentication. In this authentication, for example, whether or not it is the wavelength of light transmitted through hemoglobin such as veins is authenticated on the basis of information acquired by near infrared rays and the like. In a case where this authentication is executed, light such as infrared light may be emitted from the display unit 2, and this reflection state may be acquired and determined.

Not limited to these, for example, the display panel 4 may emit light of various colors to authenticate the living body on the basis of reflection of the emitted light. In this case, a filter for acquiring various colors may be provided as described above, and so-called multispectral or hyperspectral information may be acquired and analyzed. For example, it is possible to make a determination on the basis of information indicating reflection from the skin specific to a living body, particularly a human, or the inside of the skin.

For the authentication of the living body, not only the acquisition by the image capturing unit 8 but also, for example, the sensing information of the touch panel 6 may be used. For example, the authentication unit 106 may determine whether or not the sensing region has elasticity in the touch panel 6 and authenticate the living body. For this, the image capturing unit 8 may be used, and it may be determined whether or not the image of the finger acquired by the image capturing unit 8 has elasticity in terms of time. The elasticity may be determined on the basis of, for example, a change in the shape or size of the region occupied by the finger. Furthermore, the touch panel 6 may include a pressure-sensitive sensor, and the elasticity may be determined on the basis of the sensing information of the pressure-sensitive sensor.

Furthermore, the authentication accuracy may be enhanced by acquiring the fingerprint information at a plurality of timings. For example, the image capturing unit 8 may acquire fingerprint information at a plurality of timings, and the fingerprint information may be accumulated in the frame memory 105. Then, the authentication may be executed using the accumulated fingerprint information. For example, a defect and the like of an image generated at the time of image acquisition may be corrected by referring to the fingerprint information. More simply, after adjusting the position and angle of the fingerprint, a weighted average of fingerprint information obtained for each time may be obtained. Then, the fingerprint information acquired by the average calculation may be set as an authentication target.

The image capturing unit 8 may include other filters. For example, polarized fingerprint information can be acquired by providing a polarizing filter in the light receiving pixel. The unevenness of the fingerprint can be more clearly acquired by acquiring the polarized information. The information processing unit 10 may combine such polarized information to extract a feature point.

Furthermore, even if the image capturing unit 8 operates as a global filter, motion blur and the like may occur due to the shutter speed. In order to cope with this motion blur, the information processing unit 10 may include an image correction unit that performs degradation correction on the image included in the frame memory 105.

As described above, according to the present embodiment, it is possible to realize highly accurate personal authentication by using a camera module under the display. Moreover, impersonation can be prevented by authenticating that the authenticated subject is a human body. Furthermore, since the image capturing unit 8 can acquire an image by the operation of the rolling shutter, it is possible to realize robust fingerprint authentication against distortion of the rolling shutter of the image.

Note that, in the process of acquiring the corrected fingerprint information by the correction unit 110, not only the information of one frame but also the information of a plurality of frames may be corrected. In a case where the information of a plurality of frames is used, for example, the positions of the centers of gravity may be aligned in the fingerprint information of the plurality of frames. Furthermore, after the correction illustrated in FIG. 7 is performed on the plurality of frames, some feature points may be extracted and superimposed on the basis of these feature points. By overlapping in this manner, it is possible to acquire features more clearly, and the accuracy of fingerprint authentication can be improved.

Second Embodiment

In the first embodiment described above, the swipe speed of the user has been not considered. In the second embodiment, the speed of the user's finger is determined, and the correction of the fingerprint information is further executed based on the speed.

Figure 8:
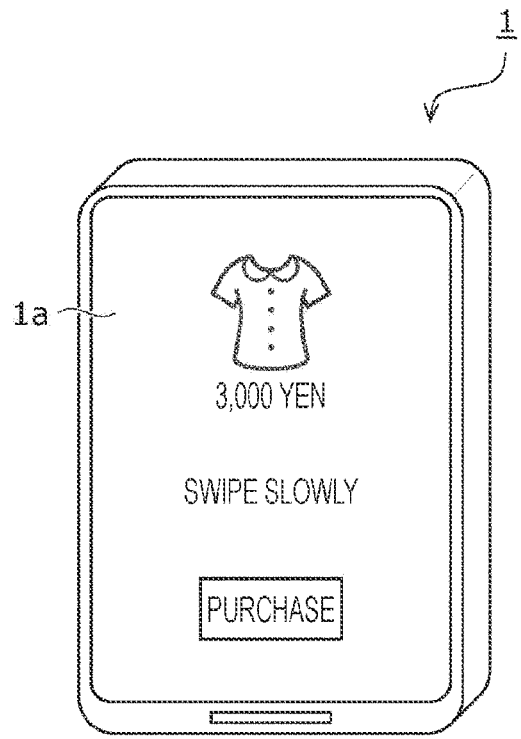
FIG. 8 is a diagram schematically illustrating an electronic device according to an embodiment.

In a case where the speed of the finger is faster than a predetermined speed, for example, as illustrated in FIG. 8, the speed detection unit 108 may output an output to urge the user to slow down the speed of the swipe to the display unit 2. Furthermore, as another example, the speed detection unit 108 may notify the output unit 107 that the speed is too fast, and output the notification to the display unit 2 via the output unit 107. Note that, in this case, the output unit 107 is not limited to display on the display unit 2, and may notify the user by sound from a speaker or vibrate a vibrator, for example.

Furthermore, the output unit 107 may determine the speed on the basis of desired authentication accuracy. In such a case, for example, in a case where high authentication accuracy is required, the output unit 107 can output to the user that the threshold for the speed detected by the speed detection unit 108 is lowered and the swiping is performed slowly in a slower speed state.

Figure 9:
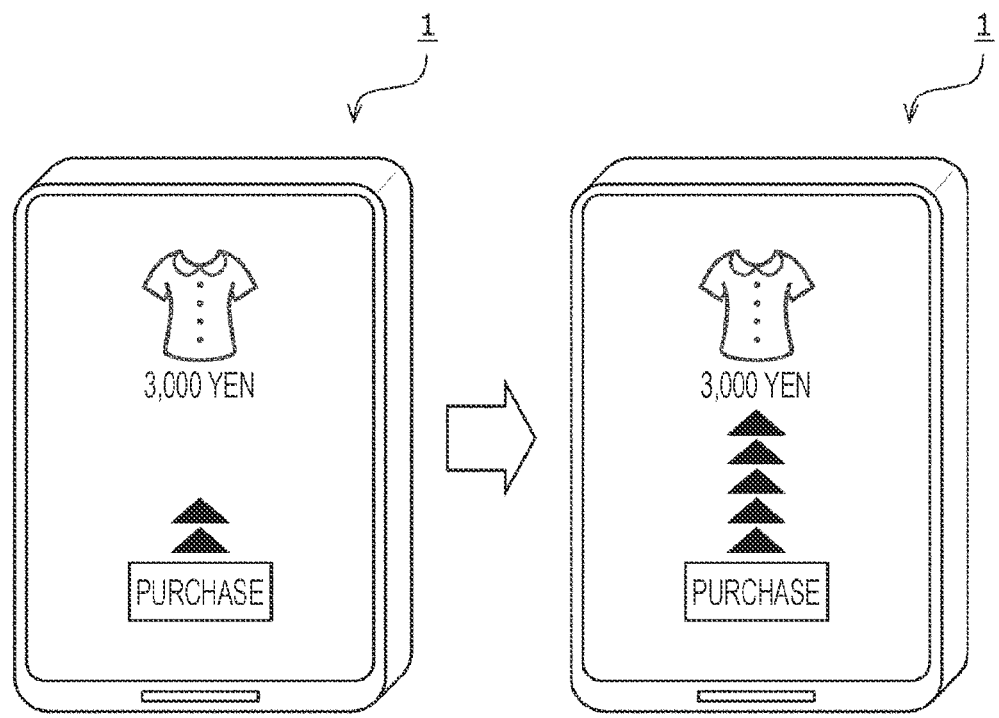
FIG. 9 is a diagram schematically illustrating an electronic device according to an embodiment.

FIG. 9 illustrates another example of the output. For example, the output unit 107 may perform display in which the number of triangle marks displayed within a predetermined time gradually increases from the left diagram to the right diagram. The increasing speed of the triangle marks may be a speed at which the image capturing unit 8 acquires fingerprint information with high accuracy. In this manner, the output unit 107 may output an index (speed guide) indicating the speed on the display. This index is not limited to a triangle as illustrated in FIG. 9, and may be, for example, a diagram in which an arrow extends, and is not limited thereto, and may be any figure, shape, and the like as long as it is an interface that indicates speed to the user.

Furthermore, although the speed detection unit 108 detects the speed on the basis of the sensing information of the touch panel 6, the present invention is not limited to this. For example, the speed may be detected on the basis of the imaging information acquired by the image capturing unit 8. For example, the speed detection unit 108 may refer to the frame memory 105 and detect the speed of the user's finger on the basis of the timing from the timing at which the image of the user's finger is acquired to the timing at which the image of the user's finger cannot be acquired, and on the basis of the size of the fingerprint acquisition region. Not limited to this, the speed may be detected by estimating how much the finger is moving after one frame or a plurality of frames from a certain time.

As described above, according to the present embodiment, by detecting the swipe speed of the user's finger, it is possible to improve the accuracy of fingerprint acquisition or the accuracy of authentication of the acquired fingerprint. Furthermore, if necessary, it is also possible to output an output that urges the user to obtain a speed suitable for fingerprint acquisition.

Note that the speed detected by the speed detection unit 108 can also be used for other purposes. For example, the camera module 3 may acquire the fingerprint information at an appropriate exposure time on the basis of the speed information. For example, the camera module 3 may shorten the exposure time in a case where the speed is slow, and may lengthen the exposure time as the speed is faster.

Third Embodiment

In the above description, authentication is realized by one finger as a representative example. For example, the authentication of the index finger may be used. Moreover, authentication using a plurality of fingers may be performed.

For example, the image capturing unit 8 may acquire not only the information of the index finger but also the information of the middle finger at the same swipe timing, and execute the personal authentication based on the two fingers. Moreover, three to five fingers may be used, or authentication may be performed with distant fingers such as an index finger and a ring finger. Of course, the index finger may not be included in the combination of the plurality of fingers.

Although the same timing is set in the above description, different timing, for example, the second authentication may be executed with the middle finger after the first authentication is executed with the index finger. In this case, information of both hands of the right hand and the left hand may be used.

In a case where information is acquired for a plurality of fingers at the same timing, information obtained by swiping the plurality of fingers may be acquired as one piece of authentication information instead of executing authentication for each finger.

As described above, authentication using any number or combination of fingers may be executed at any timing. By increasing the authentication information in this manner, it is possible to more accurately prevent erroneous detection and impersonation. The authentication by the plurality of fingers may be changed on the basis of the required level of authentication accuracy. For example, in a case where high authentication accuracy is required, a plurality of fingers may be used, or a specific combination of fingers may be used.

Fourth Embodiment

The electronic device 1 in each of the above-described embodiments is, for example, a device such as a smartphone. In a device including such a touch panel, a finger may pass on the camera module 3 at timing other than the fingerprint authentication.

Therefore, the electronic device 1 according to the present embodiment acquires such finger information at an arbitrary timing by the image capturing unit 8. Then, in a case where the authentication unit 106 can authenticate the user as a registered user, the captured fingerprint information may be stored in the storage unit 11. However, even in a case where the authentication is performed, the acquired fingerprint information may be stored in the storage unit 11 in a case where the authentication is successful.

Then, the information processing unit 10 may update the information used for authentication on the basis of the information accumulated at an arbitrary timing. For example, in a case where fingerprint information is acquired image information, information accumulated in the same direction and the same position may be calibrated, and a weighted average may be calculated such that weighting becomes heavier as new information is acquired, and the calculated weighted average may be used as information used for authentication.

Furthermore, in a case where personal authentication is performed on a predetermined finger, the finger may be acquired as information of another finger of the user at a timing when the user uses the other finger, and may be stored in the storage unit 11. By coping in this way, the authentication accuracy can be enhanced even in the case of the plurality of fingers described above.

As described above, according to the present embodiment, information used for authentication can be updated. By updating, it is possible to acquire information used for authentication, which is also applied to a subtle change in a finger (fingerprint) due to aging, a change due to environment, and the like. As a result, the accuracy of the personal authentication can be maintained high.

Fifth Embodiment

Figure 10:
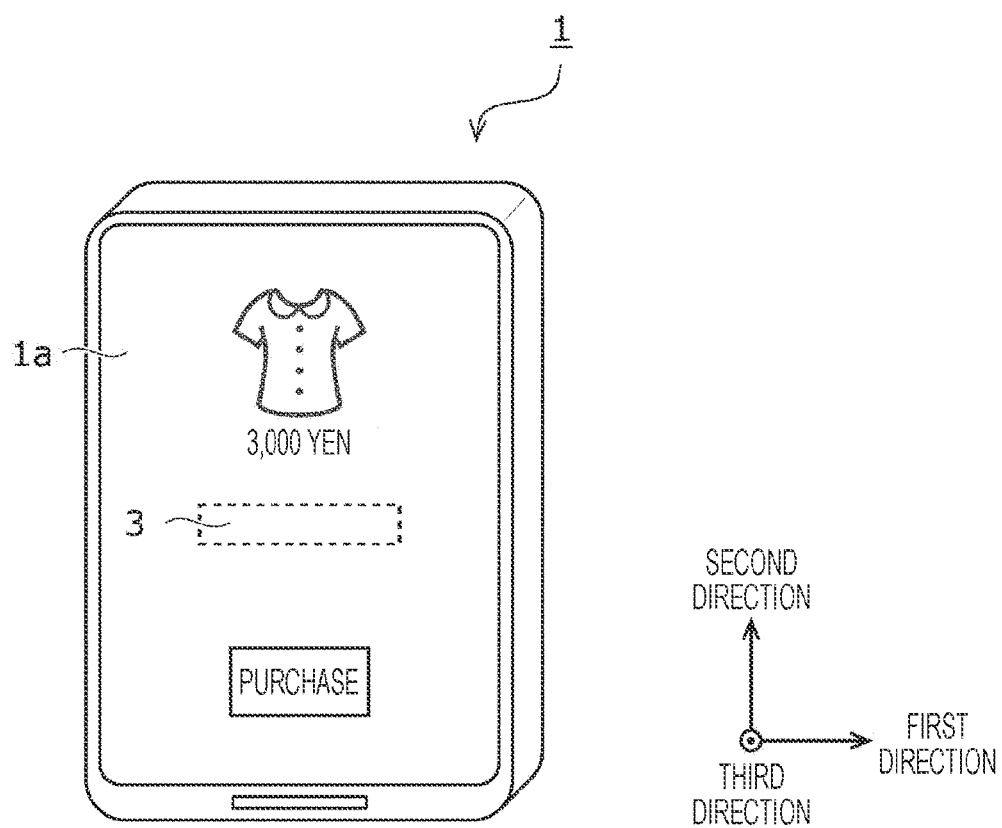
FIG. 10 is a diagram schematically illustrating an electronic device according to an embodiment.
Figure 11:
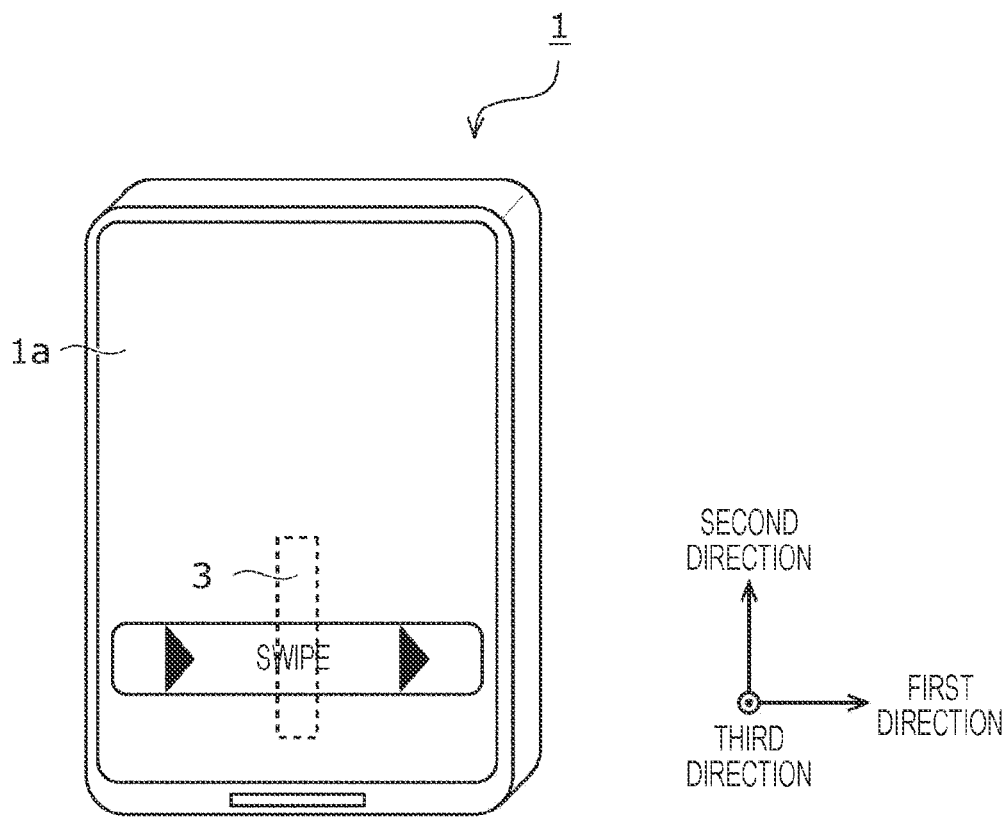
FIG. 11 is a diagram schematically illustrating an electronic device according to an embodiment.

FIGS. 10 and 11 are diagrams schematically illustrating the electronic device 1 according to the present embodiment. In the present embodiment, the camera module 3 is disposed so that the vertical direction becomes longer than the swipe direction. For example, as illustrated in FIG. 10, in a case where swiping is performed from the top to the bottom or from the bottom to the top (second direction), the camera module 3 having a region where the image capturing unit 8 is wide in the lateral direction (first direction) is used. As illustrated in FIG. 11, in a case where swiping is performed from left to right or from right to left (first direction), the camera module 3 having a region where the image capturing unit 8 is wide vertically (second direction) is used.

For example, the image capturing unit 8 can be mounted as described above by including the photoelectric conversion unit 8a (light receiving pixel) in a range indicated by a dotted line in FIGS. 10 and 11. The size of the light receiving pixel may be, for example, twice or more the number of wider disposed pixels than the number of narrower disposed pixels. For example, in FIG. 10, the number of light receiving pixels provided along the first direction may be twice or more the number of light receiving pixels provided along the second direction.

Moreover, a guide indicating the direction of the swipe may be displayed as illustrated in FIG. 11 so that the light receiving pixels crosses a certain range. As another example, a range in which fingerprint authentication can be performed by a swipe operation, that is, a range indicated by a dotted line in FIGS. 10 and 11 may be displayed on the display. By displaying in this manner, it is also possible to indicate to the user where the personal authentication can be executed by swiping.

Sixth Embodiment

An object displayed on the display unit 2 of the electronic device 1 may make the swipe region easy for the user to understand. This object may be dynamically changed.

Figure 12:
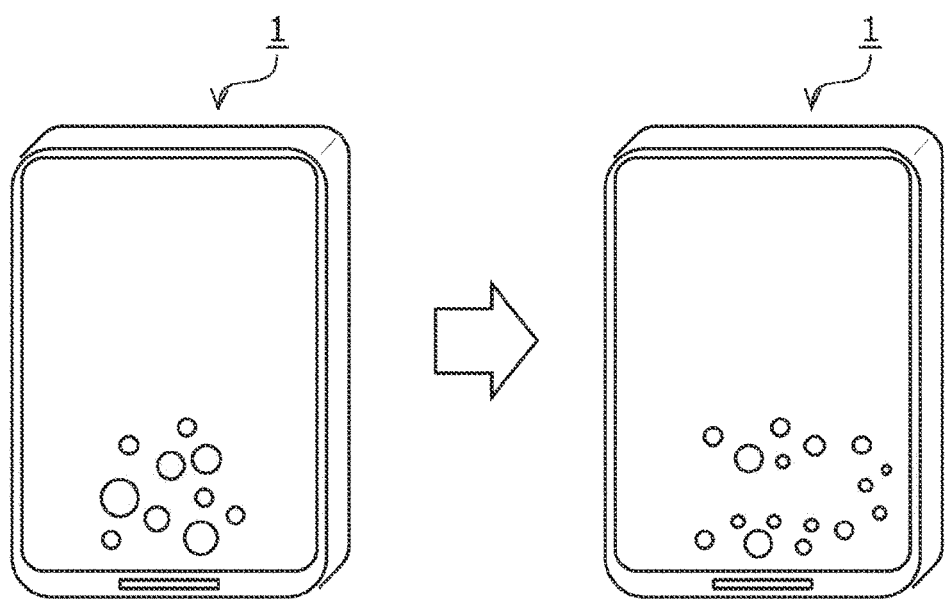
FIG. 12 is a diagram illustrating an example of a user interface of an electronic device according to an embodiment.

FIG. 12 is a diagram illustrating an example of a graphical user interface (GUI) displayed on the display unit 2 of the electronic device 1. For example, a circular object such as a water droplet is displayed on the display unit 2 as illustrated in the left diagram. Then, when the user swipes so as to cross the circular object, as illustrated in the right diagram, the object may come apart.

Furthermore, in the state of waiting for a swipe, the object in the left diagram may be shaking or moving in a predetermined region, for example, so as to more clearly indicate the swipe region. The shape and size may be changed by touching with the user's finger. Furthermore, the object may fade out after the swipe.

The display of the object is not limited to the polka dot as in FIG. 12, and for example, an object having a flow such as a river may be displayed. Such display may indicate the direction of the swipe and the like to the user. The present invention is not limited to these examples, and for example, a predetermined character may be displayed, a target may be displayed, or a display that is easy for the user to understand may be used.

When a user's finger touches the object region, the light emission state of the light emitting element may be changed.

By changing the light emission state, the wavelength of the reflected light on the display panel 4 touched by the user's finger may be changed, and the fingerprint information may be easily acquired by the change in the wavelength. For example, by setting the wavelength of the light to be emitted to a yellow to red wavelength, the color of the skin of the user or reflection from the vein may be easily understood, or conversely, by emitting light of cyan and the like having a wavelength close to a complementary color, the wavelength of the reflected light can be made suitable for acquiring fingerprint information.

Then, the object may then dynamically change on the basis of the acquisition status of the fingerprint information. For example, in a case where the fingerprint information is normally acquired, the color of the object may change, the shape may change, or the object may fade out and disappear. In a case where the fingerprint information is not normally acquired, the object in the initial state may be displayed, or the color and shape may be changed to be different from those in a case where the fingerprint information is normally acquired. Furthermore, as in the above-described embodiment, a speed guide and a location guide may be displayed. The information processing unit 10 may include a fingerprint information acquisition determination unit that determines acquisition of fingerprint information. The acquisition of the fingerprint information may be based on, for example, whether or not a predetermined number or more of unevenness and the like have been sensed in a predetermined area.

This may be based on the authentication information. For example, the object may be changed as described above in a case where the personal authentication succeeds and in a case where the personal authentication fails. Of course, a two-stage change may be performed on the basis of the acquisition status of the fingerprint information and the authentication success/failure status.

As described above, according to the present embodiment, it is also possible to widen the region where the image capturing unit 8 is present in the camera module 3 in the direction intersecting the swipe direction. By providing the optical fingerprint sensor in this manner, it is possible to mount an optical fingerprint sensor having robustness against positional deviation.

Seventh Embodiment

In the foregoing embodiments, various forms based on the speed information of the finger have been described. Moreover, in the present embodiment, the reading direction in the light receiving pixel is set as the control specification on the basis of the moving direction of the finger.

Figure 13:
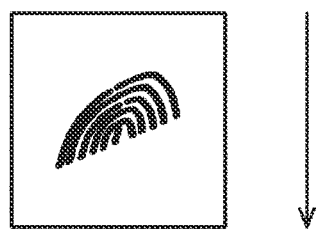
FIG. 13 is a diagram illustrating an example of image correction according to an embodiment.

FIG. 13 is an example of fingerprint information at a certain timing stored in the frame memory 105 in the present embodiment. For example, in the same situation as FIG. 7, in a case where execution is performed from the bottom to the top in which the pixels are read by the image capturing unit 8, the output signal is compressed in the vertical direction. More specifically, in a case where the finger is moving with a vector having a positive component in the upward direction of the drawing, if the pixel reading is executed from the upward direction to the downward direction, an image compressed in the vertical direction is output by the rolling shutter.

Figure 14:
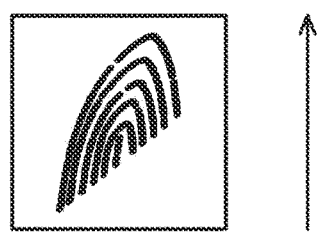
FIG. 14 is a diagram illustrating an example of image correction according to an embodiment.

With such fingerprint information, there may be a case where it is difficult for the correction unit 110 to perform correction. Therefore, in the present embodiment, the reading direction is controlled using the speed information detected by the speed detection unit 108. For example, in the speed information, in a case where the finger is a vector having a positive component from the bottom to the top of the drawing, the transfer from the light receiving pixel in the image capturing unit 8 is performed from the lower pixel to the upper pixel. By transferring in this manner, as illustrated in FIG. 14, fingerprint information can be acquired as an image expanded in the vertical direction, not as an image compressed in the vertical direction.

The fingerprint information expanded in this manner can be corrected by the correction unit 110 on the basis of the speed information, the shutter speed, and the line reading speed. More specifically, the number of first pixels to which the finger has moved while the shutter is open is estimated by the speed information and the shutter speed. Then, the number of second pixels indicating how many pixels are shifted by the rolling shutter while the shutter is open is estimated from the shutter speed and the line reading speed. Assuming that the fingerprint information is expanded by the number of first pixels and the number of second pixels, the correction unit 110 can acquire the fingerprint information having an appropriate size in the vertical direction by compressing the fingerprint information in the vertical direction.

Thereafter, similarly to the description of FIG. 7, the corrected fingerprint information is acquired. Note that, also in FIG. 7, the corrected fingerprint information may be acquired of course by compressing the fingerprint information in the vertical direction.

As described above, according to the present embodiment, it is possible to control the scanning direction of the light receiving element in the image capturing unit 8 on the basis of the moving direction of the finger and to acquire better corrected fingerprint information. The personal authentication accuracy can be further improved by using the corrected fingerprint information.

Eighth Embodiment

Figure 15:
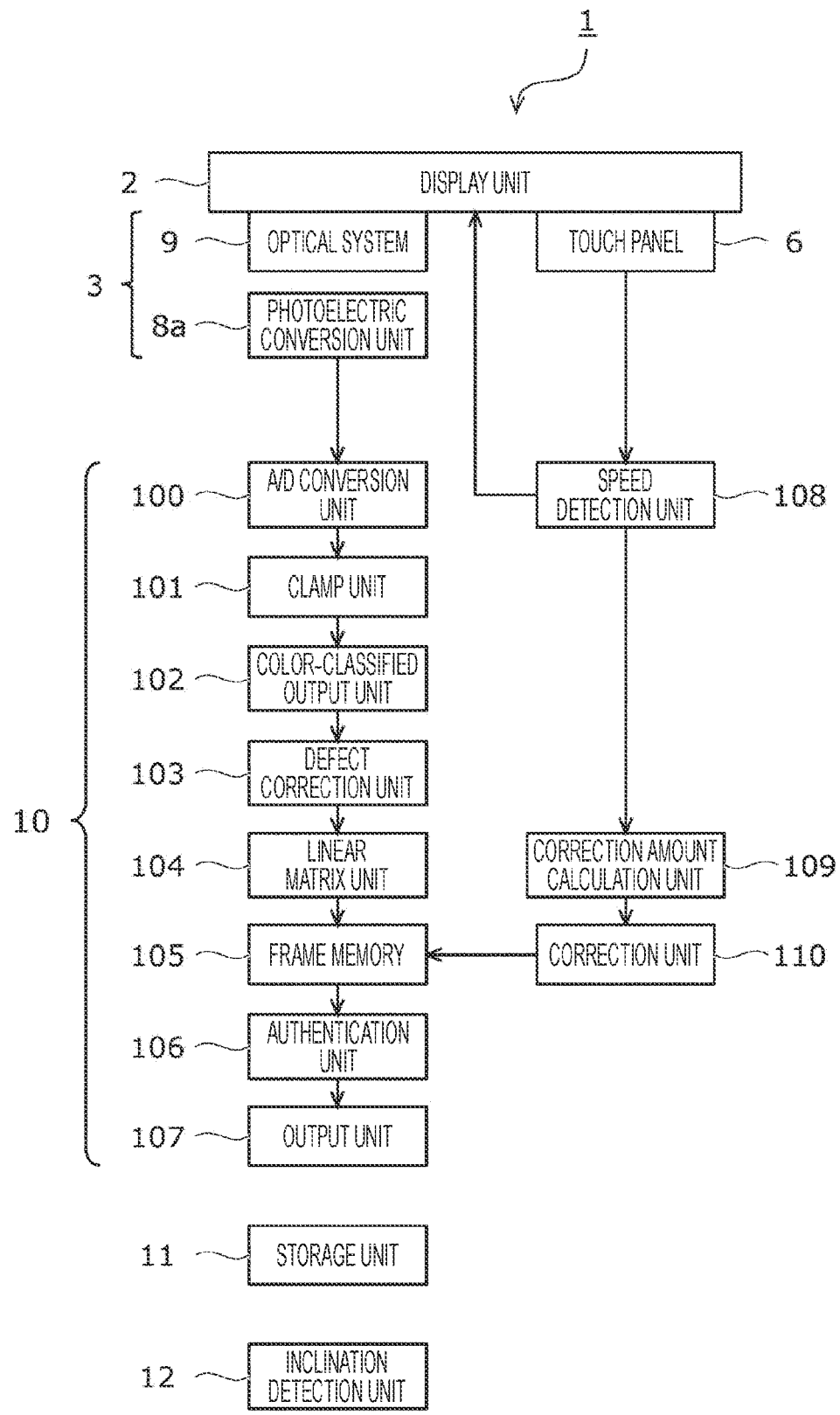
FIG. 15 is a block diagram illustrating an example of a configuration of an electronic device according to an embodiment.

FIG. 15 is a block diagram illustrating an example of the electronic device 1 according to the present embodiment. The electronic device 1 further includes an inclination detection unit 12.

The inclination detection unit 12 includes, for example, a gyroscope or an acceleration sensor. The inclination detection unit 12 detects the inclination of the electronic device 1 at the timing when the fingerprint information is acquired. The inclination is, for example, an inclination of the display with respect to gravity (vertical direction) or a horizontal direction.

Figure 16:
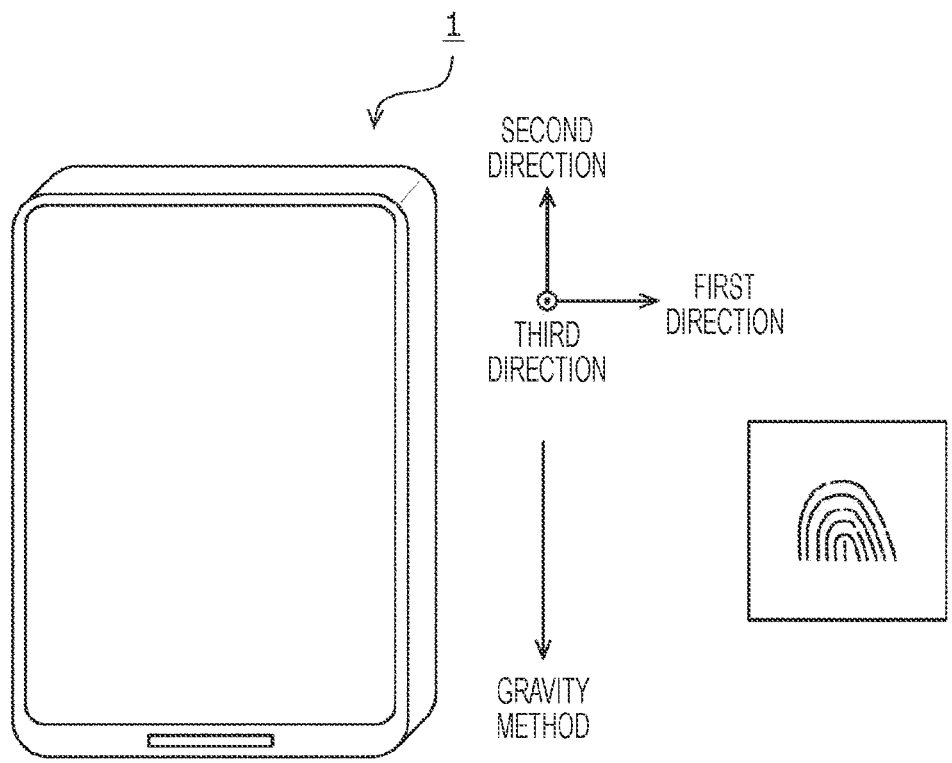
FIG. 16 is a diagram schematically illustrating an electronic device according to an embodiment.
Figure 17:
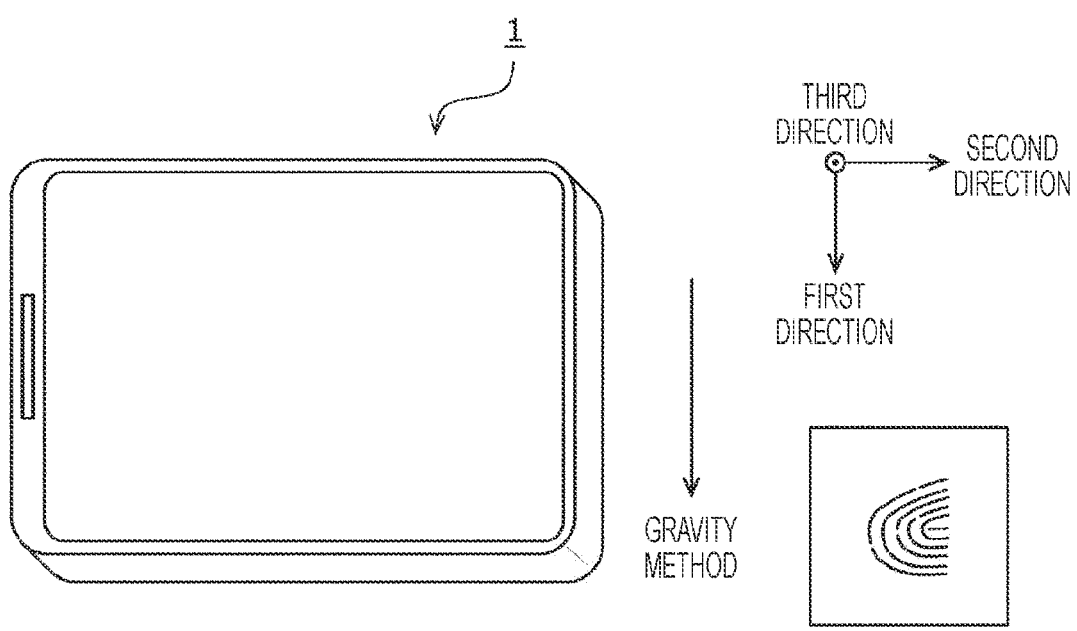
FIG. 17 is a diagram schematically illustrating an electronic device according to an embodiment.

FIGS. 16 and 17 are diagrams illustrating an example of the inclination of the electronic device 1. For example, as illustrated in FIG. 16, the first direction and the second direction in the electronic device 1 are represented as the sum of components in the gravity direction and the horizontal direction intersecting the gravity direction. In a case where the absolute value of the gravity direction component in the first direction is smaller than the absolute value of the gravity direction component in the second direction, the authentication unit 106 executes the fingerprint authentication by preferentially using the matching data in which the finger is rolled upward in the drawing illustrated in the right diagram.

On the other hand, as illustrated in FIG. 17, the absolute value of the gravity direction component in the first direction in the electronic device 1 is larger than the absolute value of the gravity direction component in the second direction, the authentication unit 106 executes the fingerprint authentication by preferentially using matching data such that the finger is directed leftward in the drawing illustrated in the right diagram.

Furthermore, the magnitude in the gravity direction in each direction and the reference sign may be used. In this case, for example, the fingerprint authentication can be executed by preferentially using matching data obtained by rotating the fingerprint by 90 degrees depending on which of the four sides is located below.

As described above, according to the present embodiment, by selecting or preferentially selecting matching data according to the inclination with respect to gravity, it is possible to improve the accuracy of matching or the speed of matching. As an example, every 180 degrees or every 90 degrees has been described, but the span of the angle may be smaller.

Furthermore, although the matching pattern has been selected, the present invention is not limited thereto. For example, the personal authentication process may be executed by rotating the corrected fingerprint information on the basis of the result of the inclination detection.

Ninth Embodiment

Figure 18:
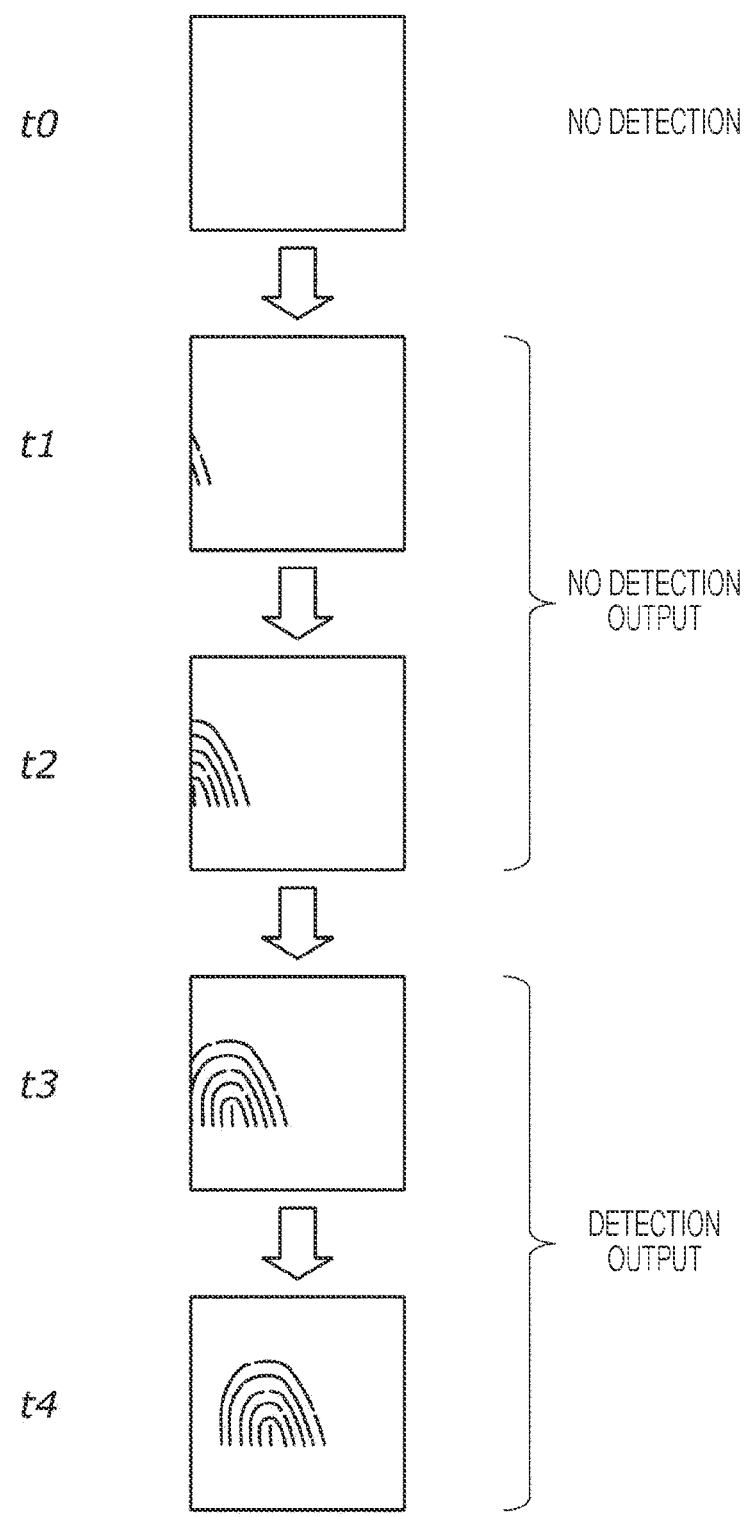
FIG. 18 is a diagram illustrating an example of reading fingerprint information according to an embodiment.

FIG. 18 is a diagram illustrating an example of acquisition of fingerprint information according to the present embodiment. t0 to t4 described on the right side of the drawing represent time, and time transitions such as t0<t1<t2<t3<t4. That is, in FIG. 18, time transitions from the upper diagram to the lower diagram.

At time t=t0, since no fingerprint is detected, the image capturing unit 8 does not output a signal.

At times t=t1 and t2, although the fingerprint is detected, the fingerprint in a sufficient range used for authentication has not been acquired, and thus the image capturing unit 8 does not output a signal to the information processing unit 10. For example, the image capturing unit 8 may determine transfer of a signal to the information processing unit 10 on the basis of an accumulated value of signals acquired in the image capturing unit 8. In this manner, the amount of data included in the fingerprint information may be estimated in the image capturing unit 8, and the transfer may be determined. The estimation of the amount of data may be executed by image analysis.

As another example, it may be determined whether or not to perform transfer by using position information of a finger on the touch panel 6 or information such as a contact area of a finger on a display surface overlapping the image capturing unit 8. The sufficient range may be a preset range, for example, a range determined on the basis of the authentication accuracy in the fingerprint.

At times t=t3 and t4, since the fingerprint is detected in a sufficient range, the analog signal is transferred from the image capturing unit 8 to the information processing unit 10. In this range, the personal authentication can be realized with sufficient accuracy. That is, the transfer of the fingerprint information from the image capturing unit 8 may be performed in a case where the fingerprint information has an amount of data of a predetermined value or more, and may not be performed in other cases.

In order to avoid the influence of rolling shutter, the sensor may be set to a high frame rate. For example, in a situation where it is sufficient that the processing in the information processing unit 10 is executed at about 30 frame per second (FPS) to 60 FPS, the frame rate of the image capturing unit 8 is set to about 100 FPS or more. The frame rate of the image capturing unit 8 may be limited by a transfer rate by physical implementation such as a bus, a transfer rate by processing in the information processing unit 10, and the like. In such a case, it may be difficult to transfer all the data to the storage unit 11 or the frame memory 105. Furthermore, in a case where information is acquired at a frame rate higher than this transfer rate, there is no guarantee that all information can be appropriately transferred to the information processing unit 10.

Therefore, in a case where the frame rate of the image capturing unit 8 is set to a high frame rate as described above, transfer of information from the image capturing unit 8 to the information processing unit 10 may be executed after it is determined that fingerprint information has been acquired in a sufficient range as described above.

As described above, according to the present embodiment, even in a case where the image capturing unit 8 acquires an image at a high frame rate to prevent rolling shutter distortion, it is possible to ensure appropriate authentication accuracy by determining whether or not fingerprint information in a range sufficient for use in authentication has been acquired and transferring a signal on the basis of the determination result. This sufficient range may be defined on the basis of information such as a predetermined region, area, and the like, or may be adaptively changed by the information processing unit 10 on the basis of a past authentication result.

Note that, in each of the above-described embodiments, it has been described as "correction", but in the present embodiment, this determination of information acquisition may be included in the concept of "correction" in a broad sense. That is, it is a concept that can be substituted for the correction of each embodiment described above in the sense that the timing of acquiring the fingerprint information is corrected in the time axis direction with respect to the acquisition of the fingerprint information in a predetermined time or between a plurality of predetermined frames.

Note that the present technology can have the following configurations.

(1)

An electronic device including:

a display;

an optical fingerprint sensor; and an information processing unit, in which the display includes a display surface having light emitting pixels in an array in a first direction and a second direction intersecting the first direction, the optical fingerprint sensor includes an imaging element including light receiving elements in an array in the first direction and the second direction on a side opposite to the display surface of the display in a third direction intersecting the first direction and the second direction, and acquires fingerprint information of fingerprint moving in contact with the display, and the information processing unit acquires corrected fingerprint information from the fingerprint information acquired by the optical fingerprint sensor.

(2)

The electronic device according to (1), in which the information processing unit corrects the fingerprint information acquired during an operation including at least a finger swipe operation.

(3)

The electronic device according to (2), further including:

a touch panel configured to sense contact information on the display, in which the information processing unit estimates an operation speed from the contact information and acquires the corrected fingerprint information on the basis of the operation speed.

(4)

The electronic device according to (3), in which
the information processing unit selects one of the fingerprint information in the fingerprint information of a plurality of frames, and aggregates the fingerprint information of another frame to the selected fingerprint information.

(5)

The electronic device according to (3) or (4), in which
the information processing unit determines an exposure time of the optical fingerprint sensor on the basis of the estimated operation speed.

(6)

The electronic device according to any one of (2) to (5), in which
the information processing unit determines a reading direction of the imaging element in the optical fingerprint sensor on the basis of a direction of the estimated operation speed.

(7)

The electronic device according to any one of (5) to (6), in which
an instruction to slow down a speed of the swipe operation is output on the basis of the requested authentication accuracy.

(8)

The electronic device according to (7), in which
an instruction of the speed of the swipe operation is output to the display.

(9)

The electronic device according to (7) or (8), in which the instruction displays a speed guide on the display.

(10)

The electronic device according to any one of (7) to (9), in which
in a case where the speed is faster than a predetermined speed, that the speed is too fast is output.

(11)

The electronic device according to (10), in which
the output that the speed is too fast is at least one of an output to the display, an output in sound, or an output in vibration.

(12)

The electronic device according to (5), in which
the information processing unit shortens an exposure time of the optical fingerprint sensor in a case where the speed is faster than a predetermined speed.

(13)

The electronic device according to any one of (1) to (12), in which
the light emitting pixel outputs light of different wavelengths on the display surface side of the light receiving element, and
the light receiving element acquires the fingerprint information on the basis of reflected light of different wavelengths.

(14)

The electronic device according to any one of (1) to (13), further including:
a polarizing filter between the light receiving element and the display surface, in which
the light receiving element senses polarized light through the polarizing filter.

(15)

The electronic device according to any one of (1) to (14), further including:
a filter configured to acquire a state of hemoglobin between the light receiving element and the display surface, in which
the information processing unit acquires information of the hemoglobin and performs biometric authentication.

(16)

The electronic device according to any one of (1) to (15), in which
the information processing unit performs biometric authentication on the basis of information on a temporal shape change of a finger in contact with the display surface.

(17)

The electronic device according to any one of (2) to (16), in which
the light receiving element detects operations of a plurality of fingers.

(18)

The electronic device according to (17), in which
the information processing unit executes the fingerprint authentication by using a combination of a plurality of fingers in an operation of a plurality of fingers.

(19)

The electronic device according to (18), in which
the combination of the plurality of fingers is different on the basis of a requested authentication accuracy.

(20)

The electronic device according to any one of (1) to (19), in which
the information processing unit detects finger information and accumulates the fingerprint information during execution of authentication or during non-execution of authentication.

(21)

The electronic device according to (20), in which
the information processing unit accumulates a change of a finger to improve authentication accuracy.

(22)

The electronic device according to (20) or (21), in which
the information processing unit acquires and accumulates the fingerprint information of a finger other than an unregistered finger.

(23)

The electronic device according to any one of (2) to (12), in which
in the light receiving elements, a number of elements in a direction intersecting a direction of the swipe operation is larger than a number of elements in the direction of the swipe operation.

(24)

The electronic device according to (23), in which
in the light receiving elements, a number of elements in a direction intersecting a direction of the swipe operation is larger than twice a number of elements in the direction of the swipe operation.

(25)

The electronic device according to (23) or (24), in which
a guide on which the swipe operation is executed in a direction intersecting a direction in which a large number of the light receiving elements are provided is displayed on the display.

(26)

The electronic device according to any one of (2) to (12), further including:

an interface that displays, on the display, a region in which the light receiving element is provided, arranges product information and a purchase button so as to pass through the region, and enables purchase of the product by performing the swipe operation on the product information from the product information to the purchase button, in which the purchase information is transmitted to a server on the basis of a result of the fingerprint authentication.

(27)

The electronic device according to (1) to (26), in which on the display, a dynamic object is displayed so as to include a region in which the light receiving element is provided.

(28)

The electronic device according to (27), in which the object changes in shape when touched by a user's finger.

(29)

The electronic device according to (27), in which a light emission state of the object changes when a user's finger touches the object.

(30)

The electronic device according to (29), in which the light emission state changes to be suitable for obtaining the fingerprint information.

(31)

The electronic device according to any one of (27) to (30), in which the object dynamically changes on the basis of an acquisition status of the fingerprint information or a personal authentication status after a user's finger passes through the object.

(32)

The electronic device according to any one of (1) to (31), further including:

an inclination detection unit configured to detect an inclination of the display from a horizontal direction, in which authentication of the fingerprint information is executed on the basis of the inclination detected by the inclination detection unit.

(33)

The electronic device according to any one of (1) to (32), in which the optical fingerprint sensor acquires the fingerprint information at a frame rate higher than a transfer rate to the information processing unit, and transfers the fingerprint information to the information processing unit in a case where the fingerprint information has an information amount of a predetermined information amount or more.

(34)

The electronic device according to (33), in which an imaging speed of the optical fingerprint sensor is a frame rate of 100 frame per second (FPS) or more.

(35)

The electronic device according to (33) or (34), in which in the optical fingerprint sensor, an amount of data included in the fingerprint information is estimated, and the fingerprint information is transferred to the information processing unit in a case where the amount of data exceeds a predetermined value.

(36)

The electronic device according to (35), in which the optical fingerprint sensor estimates the amount of data by image analysis.

(37)

The electronic device according to (35), in which the optical fingerprint sensor estimates the amount of data on the basis of information of a touch panel.

Aspects of the present disclosure are not limited to the above-described individual embodiments, but include various modifications that can be conceived by those skilled in the art, and the effects of the present disclosure are not limited to the above-described contents. That is, various additions, modifications, and partial deletions can be made without departing from the conceptual idea and spirit of the present disclosure derived from the contents defined in the claims and equivalents thereof.

REFERENCE SIGNS LIST

1 Electronic device
2 Display unit
3 Camera module
4 Display panel
5 Circularly polarizing plate
6 Touch panel
7 Cover glass
8 Image capturing unit
8a Photoelectric conversion unit
9 Optical system
10 Information processing unit
100 A/D converter
101 Clamp unit
102 Color-classified output unit
103 Defect correction unit
104 Linear matrix unit
105 Frame memory
106 Authentication unit
107 Output unit
108 Speed detection unit
109 Correction amount calculation unit
110 Correction unit
11 Storage unit
12 Inclination detection unit

The invention claimed is:

1. An electronic device, comprising:
a display;
an optical fingerprint sensor; and
an information processing unit, wherein
the display includes a display surface having light emitting pixels in an array in a first direction and a second direction intersecting the first direction,
the optical fingerprint sensor includes an imaging element including light receiving elements in an array in the first direction and the second direction on a side opposite to the display surface of the display in a third direction intersecting the first direction and the second direction, and configured to acquire fingerprint information of fingerprint moving in contact with the display, and
the information processing unit is configured to:
acquire corrected fingerprint information from the fingerprint information acquired by the optical fingerprint sensor, and
perform biometric authentication based on information on a temporal shape change of a finger in contact with the display surface.

2. The electronic device according to claim 1, wherein
the information processing unit is configured to correct the fingerprint information acquired during an operation including at least a finger swipe operation.

3. The electronic device according to claim 2, further comprising:
a touch panel configured to sense contact information on the display, wherein
the information processing unit is configured to estimate an operation speed from the contact information and acquire the corrected fingerprint information based on the operation speed.

4. The electronic device according to claim 3, wherein the information processing unit is configured to select one of the fingerprint information in the fingerprint information of a plurality of frames, and aggregate the fingerprint information of another frame to the selected fingerprint information.

5. The electronic device according to claim 3, wherein the information processing unit is configured to determine an exposure time of the optical fingerprint sensor based on the estimated operation speed.

6. The electronic device according to claim 5, wherein an instruction to slow down a speed of the finger swipe operation is output based on an authentication accuracy.

7. The electronic device according to claim 6, wherein an instruction of the speed of the finger swipe operation is output to the display.

8. The electronic device according to claim 7, wherein an output related to the speed of the finger swipe operation is at least one of an output to the display, an output in sound, or an output in vibration.

9. The electronic device according to claim 2, wherein the information processing unit is configured to determine a reading direction of the imaging element in the optical fingerprint sensor based on a direction of the estimated operation.

10. The electronic device according to claim 2, wherein each of the light receiving elements is configured to detect operations of a plurality of fingers.

11. The electronic device according to claim 2, wherein in the light receiving elements, a number of elements in a direction intersecting a direction of the finger swipe operation is larger than a number of elements in the direction of the finger swipe operation.

12. The electronic device according to claim 2, wherein a guide on which the finger swipe operation is executed in a direction intersecting a direction in which a large number of the light receiving elements are provided, is displayed on the display.

13. The electronic device according to claim 2, further comprising:
an interface that is configured to:
display, on the display, a region in which each of the light receiving elements is provided,
arrange product information and a purchase button so as to pass through the region, and
enable purchase of a product based on the finger swipe operation, on the product information, from the product information to the purchase button, wherein
purchase information is transmitted to a server based on a result of authentication of the fingerprint.

14. The electronic device according to claim 1, wherein the light emitting pixel is configured to output light of different wavelengths on a side of the display surface of the light receiving elements, and
each of the light receiving elements is configured to acquire the fingerprint information based on a reflected light of different wavelengths.

15. The electronic device according to claim 1, further comprising:
a polarizing filter between the light receiving elements and the display surface, wherein
each of the light receiving elements is configured to sense polarized light through the polarizing filter.

16. The electronic device according to claim 1, further comprising:
a filter configured to acquire a state of hemoglobin between the light receiving elements and the display surface, wherein
the information processing unit is configured to acquire information of the hemoglobin and perform the biometric authentication.

17. The electronic device according to claim 1, wherein the information processing unit is configured to detect finger information and accumulate the fingerprint information during execution of authentication or during non-execution of authentication.

18. The electronic device according to claim 1, further comprising:
an inclination detection unit configured to detect an inclination of the display from a horizontal direction, wherein
authentication of the fingerprint information is executed based on the inclination detected by the inclination detection unit.

19. The electronic device according to claim 1, wherein the optical fingerprint sensor is configured to:
acquire the fingerprint information at a frame rate higher than a transfer rate to the information processing unit, and
transfer the fingerprint information to the information processing unit based on a determination that the fingerprint information has an information amount of a predetermined information amount or more.

* * * * *